(12) United States Patent
Clifford et al.

(10) Patent No.: US 9,655,648 B2
(45) Date of Patent: May 23, 2017

(54) FEMORAL AND TIBIAL BASE COMPONENTS

(75) Inventors: Anton G. Clifford, Mountain View, CA (US); Joshua Makower, Los Altos, CA (US); Michael E. Landry, Austin, TX (US); Clinton N. Slone, San Francisco, CA (US)

(73) Assignee: MOXIMED, INC., Hayward, CA (US)

( * ) Notice: Subject to any disclaimer, the term of this patent is extended or adjusted under 35 U.S.C. 154(b) by 873 days.

(21) Appl. No.: 12/112,415

(22) Filed: Apr. 30, 2008

(65) Prior Publication Data

US 2008/0275562 A1 Nov. 6, 2008

Related U.S. Application Data

(63) Continuation-in-part of application No. 11/743,097, filed on May 1, 2007, and a continuation-in-part of
(Continued)

(51) Int. Cl.
*A61B 17/56* (2006.01)
*A61B 17/68* (2006.01)
(Continued)

(52) U.S. Cl.
CPC ............ *A61B 17/68* (2013.01); *A61F 2/0811* (2013.01); *A61B 17/6425* (2013.01);
(Continued)

(58) Field of Classification Search
CPC ...................................................... A61B 17/56
(Continued)

(56) References Cited

U.S. PATENT DOCUMENTS 2,632,440 A 3/1953 Hauser
2,877,033 A 3/1959 Koetke
(Continued)

FOREIGN PATENT DOCUMENTS

CA 1205602 6/1986
DE 19855254 6/2000
(Continued)

OTHER PUBLICATIONS

Aldegheri, Roberto, M.D. et al.; "Articulated Distraction of the Hip-Conservative Surgery for Arthritis in Young Patients", Clinical Orthopaedics and Related Research, No. 301, pp. 94-101.
(Continued)

*Primary Examiner* — Christopher D Prone
(74) *Attorney, Agent, or Firm* — Adam J. Cermak; Cermak Nakajima & McGowan LLP

(57) ABSTRACT

Various embodiments are directed to base components that are usable with implantable mechanical energy absorbing systems. According to one embodiment, the base component includes a low-profile body having a elongate, straight portion at a first end and a curved body portion at a second end. The second end is elevated as compared to the first end. An inner surface of the low-profile body has a raised portion extending along the elongate, straight portion of the low-profile body. The base component also includes a plurality of openings positioned along the low-profile body for alignment and purposes of affixation to body anatomy.

25 Claims, 21 Drawing Sheets

Related U.S. Application Data application No. 11/743,605, filed on May 2, 2007, and a continuation-in-part of application No. 11/775,139, filed on Jul. 9, 2007, now Pat. No. 7,611,540, and a continuation-in-part of application No. 11/775,149, filed on Jul. 9, 2007, now Pat. No. 7,655,041, and a continuation-in-part of application No. 11/775,145, filed on Jul. 9, 2007, now Pat. No. 7,678,147.

(51) Int. Cl.
    *A61B 17/64* (2006.01)
    *A61B 17/80* (2006.01)
    *A61F 2/08* (2006.01)

(52) U.S. Cl.
    CPC ......... *A61B 17/809* (2013.01); *A61B 17/8061* (2013.01); *A61B 17/8085* (2013.01); *A61F 2/08* (2013.01); *A61F 2002/0829* (2013.01); *A61F 2002/0864* (2013.01); *A61F 2002/0888* (2013.01)

(58) Field of Classification Search
    USPC ..... 606/69, 71, 287, 293, 294, 88, 282, 286; 623/20.19, 20.21, 20.24–20.26
    See application file for complete search history.

(56) References Cited

U.S. PATENT DOCUMENTS

| | | | |
|---|---|---|---|
| 3,242,922 A | 3/1966 | Thomas | |
| 3,407,409 A | 10/1968 | Prahl | |
| 3,648,294 A | 3/1972 | Shahrestani | |
| 3,681,786 A | 8/1972 | Lynch | |
| 3,779,654 A | 12/1973 | Horne | |
| 3,875,594 A | 4/1975 | Swanson | |
| 3,902,482 A * | 9/1975 | Taylor | 602/16 |
| 3,988,783 A | 11/1976 | Treace | |
| 3,990,116 A | 11/1976 | Fixel et al. | |
| 4,187,841 A | 2/1980 | Knutson | |
| 4,246,660 A * | 1/1981 | Wevers | 623/13.13 |
| 4,308,863 A | 1/1982 | Fischer | |
| 4,353,361 A | 10/1982 | Foster | |
| 4,501,266 A | 2/1985 | McDaniel | |
| 4,570,625 A | 2/1986 | Harris | |
| 4,576,158 A | 3/1986 | Boland | |
| 4,621,627 A | 11/1986 | DeBastiani et al. | |
| 4,637,382 A | 1/1987 | Walker | |
| 4,696,293 A | 9/1987 | Ciullo | |
| 4,759,765 A | 7/1988 | Van Kampen | |
| 4,769,011 A | 9/1988 | Swaniger | |
| 4,776,851 A | 10/1988 | Bruchman et al. | |
| 4,846,842 A | 7/1989 | Connolly et al. | |
| 4,851,005 A * | 7/1989 | Hunt et al. | 623/13.11 |
| 4,863,475 A | 9/1989 | Andersen et al. | |
| 4,871,367 A | 10/1989 | Christensen et al. | |
| 4,923,471 A | 5/1990 | Morgan | |
| 4,942,875 A | 7/1990 | Hlavacek et al. | |
| 4,959,065 A | 9/1990 | Arnett et al. | |
| 4,988,349 A | 1/1991 | Pennig | |
| 5,002,574 A | 3/1991 | May et al. | |
| 5,011,497 A | 4/1991 | Persson et al. | |
| 5,019,077 A | 5/1991 | De Bastiani et al. | |
| 5,026,372 A | 6/1991 | Sturtzkopf et al. | |
| 5,041,112 A | 8/1991 | Mingozzi et al. | |
| 5,100,403 A | 3/1992 | Hotchkiss et al. | |
| 5,103,811 A | 4/1992 | Crupi | |
| 5,121,742 A | 6/1992 | Engen | |
| 5,152,280 A | 10/1992 | Danieli | |
| 5,234,435 A | 8/1993 | Seagrave, Jr. | |
| 5,316,546 A | 5/1994 | Lindh et al. | |
| 5,318,567 A | 6/1994 | Vichard | |
| 5,352,190 A | 10/1994 | Fischer | |
| 5,375,823 A | 12/1994 | Navas | |
| 5,405,347 A | 4/1995 | Lee et al. | |
| 5,415,661 A | 5/1995 | Holmes | |
| 5,540,688 A | 7/1996 | Navas | |
| 5,575,819 A | 11/1996 | Amis | |
| 5,578,038 A | 11/1996 | Slocum | |
| 5,601,553 A | 2/1997 | Trebing et al. | |
| 5,624,440 A | 4/1997 | Huebner | |
| 5,662,648 A | 9/1997 | Faccioli et al. | |
| 5,662,650 A | 9/1997 | Bailey et al. | |
| 5,681,313 A | 10/1997 | Diez | |
| 5,695,496 A | 12/1997 | Orsak et al. | |
| 5,716,357 A | 2/1998 | Rogozinski | |
| 5,803,924 A | 9/1998 | Oni et al. | |
| 5,873,843 A | 2/1999 | Draper | |
| 5,928,234 A | 7/1999 | Manspeizer | |
| 5,976,125 A | 11/1999 | Graham | |
| 5,976,136 A | 11/1999 | Bailey et al. | |
| 5,993,449 A | 11/1999 | Schlapfer | |
| 5,993,486 A | 11/1999 | Tomatsu | |
| 6,036,691 A | 3/2000 | Richardson | |
| 6,113,637 A | 9/2000 | Gill et al. | |
| 6,139,550 A | 10/2000 | Michelson | |
| 6,162,223 A * | 12/2000 | Orsak et al. | 606/59 |
| 6,176,860 B1 | 1/2001 | Howard | |
| 6,197,030 B1 | 3/2001 | Pham | |
| 6,264,696 B1 | 7/2001 | Reigner et al. | |
| 6,277,124 B1 | 8/2001 | Haag | |
| 6,315,852 B1 | 11/2001 | Magrini et al. | |
| 6,355,037 B1 | 3/2002 | Crosslin et al. | |
| 6,364,881 B1 | 4/2002 | Apgar et al. | |
| 6,409,729 B1 | 6/2002 | Martinelli et al. | |
| 6,482,232 B1 | 11/2002 | Boucher et al. | |
| 6,494,914 B2 | 12/2002 | Brown et al. | |
| 6,527,733 B1 | 3/2003 | Ceriani et al. | |
| 6,540,708 B1 * | 4/2003 | Manspeizer | 602/16 |
| 6,572,653 B1 | 6/2003 | Simonson | |
| 6,599,322 B1 | 7/2003 | Amrich et al. | |
| 6,620,332 B2 | 9/2003 | Amrich | |
| 6,623,486 B1 | 9/2003 | Weaver et al. | |
| 6,663,631 B2 | 12/2003 | Kuntz | |
| 6,679,921 B2 | 1/2004 | Grubbs | |
| 6,692,497 B1 | 2/2004 | Tormala et al. | |
| 6,692,498 B1 | 2/2004 | Niiranen et al. | |
| 6,752,831 B2 | 6/2004 | Sybert et al. | |
| 6,884,242 B2 | 4/2005 | LeHuec et al. | |
| 6,966,910 B2 | 11/2005 | Ritland | |
| 6,972,020 B1 | 12/2005 | Grayson et al. | |
| 6,997,940 B2 | 2/2006 | Bonutti | |
| 7,018,418 B2 | 3/2006 | Amrich et al. | |
| 7,029,475 B2 | 4/2006 | Pajabi | |
| 7,128,744 B2 | 10/2006 | Weaver et al. | |
| 7,141,073 B2 | 11/2006 | May et al. | |
| 7,188,626 B2 | 3/2007 | Foley et al. | |
| 7,201,728 B2 | 4/2007 | Sterling | |
| 7,235,077 B1 | 6/2007 | Wang et al. | |
| 7,235,102 B2 | 6/2007 | Ferree et al. | |
| 7,238,203 B2 | 7/2007 | Bagga et al. | |
| 7,241,298 B2 | 7/2007 | Nemec et al. | |
| 7,247,157 B2 | 7/2007 | Prager et al. | |
| 7,252,670 B2 | 8/2007 | Morrison et al. | |
| 7,261,739 B2 | 8/2007 | Ralph et al. | |
| 7,273,481 B2 | 9/2007 | Lombardo et al. | |
| 7,276,070 B2 | 10/2007 | Muckter | |
| 7,282,065 B2 | 10/2007 | Kirschman | |
| 7,285,134 B2 | 10/2007 | Berry et al. | |
| 7,288,094 B2 | 10/2007 | Lindemann et al. | |
| 7,288,095 B2 | 10/2007 | Baynham et al. | |
| 7,291,150 B2 | 11/2007 | Graf | |
| 7,306,605 B2 | 12/2007 | Ross | |
| 7,322,983 B2 | 1/2008 | Harris | |
| 7,322,984 B2 | 1/2008 | Doubler et al. | |
| 7,341,589 B2 | 3/2008 | Weaver et al. | |
| 7,361,196 B2 | 4/2008 | Fallin et al. | |
| 2001/0020143 A1 | 9/2001 | Stark et al. | |
| 2002/0095154 A1 | 7/2002 | Atkinson et al. | |
| 2002/0151978 A1 | 10/2002 | Zacouto et al. | |
| 2003/0216809 A1 | 11/2003 | Ferguson | |
| 2004/0102776 A1 | 5/2004 | Huebner | |
| 2004/0260302 A1 | 12/2004 | Manspeizer | |
| 2004/0267179 A1 | 12/2004 | Leman | |

(56) References Cited

U.S. PATENT DOCUMENTS

| | | | |
|---|---|---|---|
| 2005/0049708 A1 | 3/2005 | Atkinson et al. | |
| 2005/0085815 A1 | 4/2005 | Harms et al. | |
| 2005/0119744 A1 | 6/2005 | Buskirk et al. | |
| 2005/0154390 A1 | 7/2005 | Biedermann et al. | |
| 2005/0192674 A1 | 9/2005 | Ferree | |
| 2005/0251260 A1 | 11/2005 | Gerber et al. | |
| 2005/0261680 A1 | 11/2005 | Draper | |
| 2006/0064169 A1 | 3/2006 | Ferree | |
| 2006/0085001 A1* | 4/2006 | Michelson | 606/69 |
| 2006/0167559 A1 | 7/2006 | Johnstone et al. | |
| 2006/0178744 A1 | 8/2006 | de Villiers et al. | |
| 2006/0247637 A1 | 11/2006 | Colleran et al. | |
| 2007/0043356 A1 | 2/2007 | Timm et al. | |
| 2007/0053963 A1 | 3/2007 | Hotchkiss et al. | |
| 2007/0106299 A1 | 5/2007 | Manspeizer | |
| 2007/0161993 A1 | 7/2007 | Lowery et al. | |
| 2007/0168033 A1 | 7/2007 | Kim et al. | |
| 2007/0168036 A1 | 7/2007 | Ainsworth et al. | |
| 2007/0198088 A1 | 8/2007 | Biedermann et al. | |
| 2007/0198091 A1 | 8/2007 | Boyer et al. | |
| 2007/0244483 A9 | 10/2007 | Winslow et al. | |
| 2007/0244488 A1 | 10/2007 | Metzger et al. | |
| 2007/0288014 A1 | 12/2007 | Shadduck et al. | |
| 2008/0015591 A1 | 1/2008 | Castaneda et al. | |
| 2008/0015592 A1 | 1/2008 | Long et al. | |
| 2008/0015593 A1 | 1/2008 | Pfefferle et al. | |
| 2008/0027558 A1 | 1/2008 | Palmer et al. | |
| 2008/0071373 A1 | 3/2008 | Molz et al. | |
| 2008/0071375 A1 | 3/2008 | Carver et al. | |
| 2008/0097441 A1 | 4/2008 | Hayes et al. | |
| 2008/0132954 A1 | 6/2008 | Sekhon et al. | |
| 2008/0154378 A1 | 6/2008 | Pelo | |
| 2008/0275560 A1 | 11/2008 | Clifford et al. | |

FOREIGN PATENT DOCUMENTS

| | | |
|---|---|---|
| EP | 0383419 | 8/1990 |
| EP | 0953317 | 4/1999 |
| EP | 1770302 | 4/2007 |
| EP | 1429675 | 10/2007 |
| EP | 1682020 | 10/2007 |
| EP | 1847228 | 10/2007 |
| EP | 1847229 | 10/2007 |
| EP | 1005290 | 2/2008 |
| EP | 1468655 | 5/2008 |
| GB | 1507953 | 4/1978 |
| GB | 2223406 | 4/1990 |
| GB | 2250919 | 6/1992 |
| GB | 2250919 | 10/1993 |
| JP | 59-131348 | 7/1984 |
| JP | 7-100159 | 4/1995 |
| JP | 2532346 | 4/1995 |
| JP | 2000-503865 | 4/2000 |
| JP | 2001-145647 | 4/2000 |
| JP | 2003-102744 | 5/2001 |
| JP | 2006-280951 | 10/2006 |
| JP | 2007-167318 | 7/2007 |
| JP | 2007-167319 | 7/2007 |
| JP | 2007-170969 | 7/2007 |
| RU | 2085148 | 7/1997 |
| RU | 2217105 | 11/2003 |
| RU | 2241400 | 9/2004 |
| SU | 578063 | 11/1977 |
| SU | 578957 | 11/1977 |
| SU | 624613 | 8/1978 |
| SU | 640740 | 1/1979 |
| SU | 704605 | 12/1979 |
| SU | 719612 | 3/1980 |
| SU | 741872 | 7/1980 |
| SU | 1186204 | 10/1985 |
| SU | 1251889 | 8/1986 |
| SU | 1316666 A1 | 6/1987 |
| SU | 1588404 | 8/1990 |
| SU | 1699441 A1 | 12/1991 |
| SU | 1769868 A1 | 10/1992 |
| WO | WO91/07137 | 5/1991 |
| WO | WO 94/06364 | 3/1994 |
| WO | WO 96/19944 | 7/1996 |
| WO | WO 2004019831 | 3/2004 |
| WO | WO 2004024037 | 3/2004 |
| WO | WO 2007056645 | 5/2005 |
| WO | WO2006/045091 | 4/2006 |
| WO | WO2006/049993 | 5/2006 |
| WO | WO 2006110578 | 10/2006 |
| WO | WO 2007090009 | 8/2007 |
| WO | WO 2007090015 | 8/2007 |
| WO | WO 2007090017 | 8/2007 |
| WO | WO 2007106962 | 9/2007 |
| WO | WO 2007109417 | 9/2007 |
| WO | WO 2007109436 | 9/2007 |
| WO | WO 2007114769 | 10/2007 |
| WO | WO 2007117571 | 10/2007 |
| WO | WO 2008006098 | 1/2008 |

OTHER PUBLICATIONS

Benzel, Edward; "Qualitative Attributes of Spinal Implants"; in: Biomechanics of Spine Stabilization, 1995.

Buckwalter, Joseph A.; "Joint distraction for osteoarthritis"; The Lancet, Department of Orthopaedic Surgery, University of Iowa Hospitals and Clinics, vol. 347, Feb. 3, 1996, pp. 279-280.

Coathup, M.J. et al.; "Osseo-mechanical induction of extra-cortical plates with reference to their surface properties and gemoetric designs", Elsevier, Biomaterials 20 (1999) 793-800.

Deie, Masataka, M.D. et al.; "A New Articulated Distraction Arthroplasty Device for Treatment of the Osteoarthritic Knee Joint: A Preliminary Report"; Arthroscopy: The Journal of Arthroscopic and Related Surgery; vol. 23, No. 8 (Aug. 2007): pp. 833-838.

Dienst, M. et al.; "Dynamic external fixation for distal radius fractures"; Clinical Orthopaedics and Related Research, 1997, vol. 338, pp. 160-171.

Gunther, Klaus-Peter, M.D.; "Surgical approaches for osteoarthritis"; Best Practice & Research Clinical Rheumatology, vol. 15, No. 4, pp. 627-643, 2001.

Hall, J. et al.; "Use of a hinged external fixator for elbow instability after severe distal humeral fracture"; Journal of Orthopaedic Trauma, 2000, vol. 14, No. 6, pp. 442-448.

Klein, D. et al.; "Percutaneous treatment of carpal, metacarpal, and phalangeal injuries"; Clinical Orthopaedics and Related Research, 200, vol. 375, pp. 116-125.

Krakauer, J. et al.; "Hinged device for fractures involving the proximal interphalangeal joint"; Clinical Orthopaedics and Related Research, 1996, vol. 327, pp. 29-37.

Lafeber et al., Unloading Joints to Treat Osteoarthritis, Including Joint Distraction, Current Opinion in Rheumatology 2006, 18;519-525.

Madey, S. et al.; Hinged external fixation of the elbow: optimal axis alignment to minimize motion resistance; Journal of Orthopaedic Trauma, 2000, vol. 14, No. 1, pp. 41-47.

Neel, Michael D., M.D.; "Repiphysis—Limb Salvage System for the Skeletally Immature"; Wright Medical Technology, Repiphysis Limb Salvage System, 2001, pp. 1-8.

Neel, Michael D, M.D. et al.; "Early Multicenter Experience With a Noninvasive Expandable Prosthesis"; Clinical Orthopaedics and Related Research, 2003, No. 415, pp. 72-81.

Nockels, Russ P.; "Dynamic Stabilization in the Surgical Management of Painful Lumbar Spinal Disorders"; Spine, 2005, vol. 30, No. 16S, pp. S68-S72.

Perry, Clayton R. et al.; "Patellar Fixation Protected with a Load-Sharing Cable: A Mechanical and Clinical Study"; Journal of Orthopaedic Trauma, 1988, vol. 2, No. 3, pp. 234-240.

Orthofix; "Xcaliber Articulated Ankle"; advertising brochure, May 2004.

Orthofix; "Gentle Limb Deformity Correction"; website pages, http://www.eight-plate.com/, 2008.

Pilliar et al., Bone Ingrowth and Stress Shielding with a Porous Surface Coated Fracture Fixation Plate, Journal of Biomedical Materials Research, vol. 13, 799-810 (1979).

(56) References Cited

OTHER PUBLICATIONS

Pollo, Fabian E. et al.; "Reduction of Medial Compartment Loads With Valgus Bracing of the Osteoarthritic Knee"; American Journal Sports Medicine, vol. 30, No. 3, 2002; pp. 414-421.
Repicci, John A., M.D. et al. "Minimally invasive unicondylar knee arthroplasty for the treatment of unicompartmental osteoarthritis: an outpatient arthritic bypass procedure"; Orthopedic Clinics of North America, 35 (2004), pp. 201-216.
Sommerkamp, G. et al.; "Dynamic external fixation of unstable reactures of the distal part of the radius"; The Journal of Bone and Joint Surgery; 1994, vol. 76-A, No. 8, pp. 1149-1161.
Tencer, Allan F. et al. "Fixation of the Patella (Chap. 9.3)"; in: Biomechanics in Orthopedic Trauma Bone Fracture and Fixation, 1994.
Thakur, A.J.; "Tension Band Wiring"; in; The Elements of Fracture Fixation, 1997.
Uchikura, C. et al.; "Comparative study of nonbridging and bridging external fixators fro unstable distal raduis fractures"; Journal of Orthopaedic Science, 2004, vol. 9, pp. 560-565.
Weisstein. Jason S., M.D. et al.; "Oncologic Approaches to Pediatric Limb Preservation"; Journal of the American Academy of Orthopaedic Surgeons; vol. 13, No. 8, Dec. 2005.
Wilke, Hans-Joachim et al.; "Biomechanical Evaluation of a New Total Posterior-Element Replacement System"; Spine, 2006, vol. 31, No. 24, pp. 2790-2796.
Wilkins, Ross M., M.D. et al.; "The Phenix Expandable Prosthesis"; Clinical Orthopaedics and Related Research, No. 382, pp. 51-58.
Yamamoto, Ei et al.; "Effects of Stress Shielding on the Transverse Mechanical Properties of Rabbit Patellar Tendons"; Journal of Biomechanical Engineering, 2000, vol. 122, pp. 608-614.
Lapinskaya, V.S., et al., "An Endoapparatus for Restoration of the Hip Joint", Writers Collective, 2008, UDK 615.472.03:616.728.2-089.28.
Nagai, et al., "B109 Mobility Evaluation of Hip-Joint Nonweight-Bearing Device", The Japan Society of Mechanical Engineers No. 02-26.
Tomita, Naohide, "Development of Treatment Devices for Cartilage Regeneration", BME vol. 16, No. 2.
Lentsner, A.A., et al., "Device for Functional Relief of Hip Joint in Cotyloid Cavity Fracture Cases", Ortop Travmatol Protez. Apr. 1990(4) 44-6.
Lapinskaya, Valentina Spiridonovna, "Treatment of Diseases and Injuries of Hip Joint Using a Method of Distraction", Kuibyshev Medical Institute, 1990.
Larionov d. Yu, et al., "Medical Devices", Scientific and Technical Bimonthly Journal, May-Jun. 2008.
PCT search report dated Jan. 20, 2010 from PCT application No. PCT/US2009/002714 as issued by the European Patent Office as searching authority.
Office Action from U.S. Appl. No. 12/113,164 dated Dec. 26, 2014.
Office Action from U.S. Appl. No. 12/702,599 dated Mar. 24, 2015.
Office Action from U.S. Appl. No. 13/309,984 dated Jun. 26, 2015.
Office Action from U.S. Appl. No. 13/800,676 dated Jul. 8, 2015.
Office Action from U.S. Appl. No. 12/112,659 dated Sep. 1, 2015.
Office Action from U.S. Appl. No. 14/075,090 dated Mar. 14, 2016.
Office Action from U.S. Appl. No. 11/743,605 issued Jun. 13, 2016.
Office Action from U.S. Appl. No. 14/075,090, issued Dec. 2, 2016.

\* cited by examiner

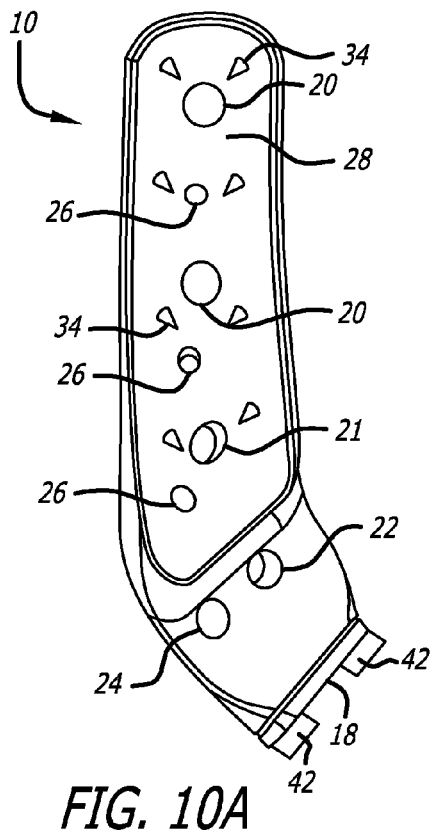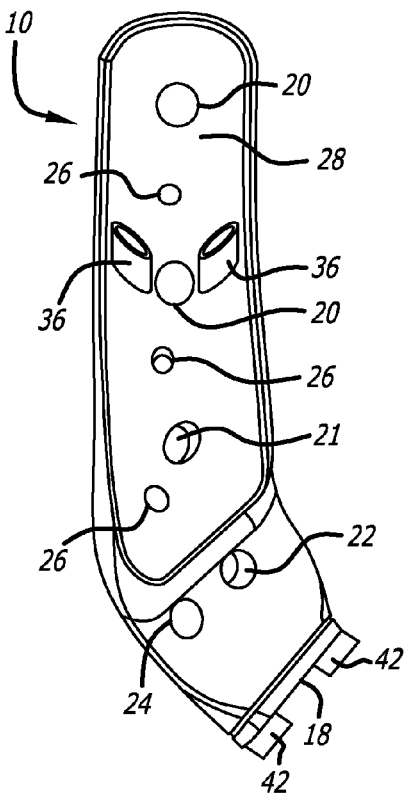
FIG. 10A
FIG. 10B
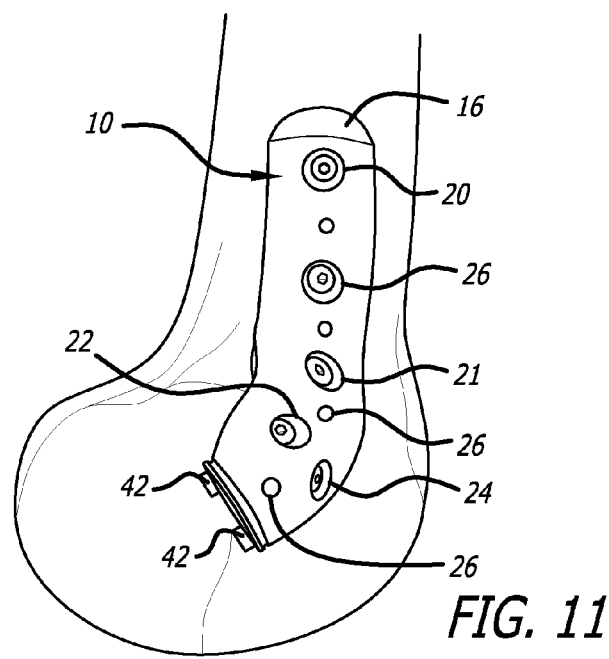
FIG. 11

FEMORAL AND TIBIAL BASE COMPONENTS

CROSS-REFERENCE TO RELATED APPLICATIONS

This application is a continuation-in-part of U.S. application Ser. No. 11/743,097, filed May 1, 2007, a continuation-in-part of U.S. application Ser. No. 11/743,605, filed May 2, 2007, a continuation-in-part of U.S. Application Ser. No. 11/775,139, filed Jul. 9, 2007, now U.S. Pat. No. 7,611,540, a continuation-in-part of U.S. Application Ser. No. 11/775,149, filed Jul. 9, 2007, now U.S. Pat. No. 7,655,041, and a continuation-in-part of U.S. application Ser. No. 11/775,145, filed Jul. 9, 2007, now U.S. Pat. No. 7,678,147, the entire disclosures of which are expressly incorporated herein by reference.

FIELD OF EMBODIMENTS

Various embodiments disclosed herein are directed to structure for attachment to body anatomy, and more particularly, towards approaches for providing mounting members for extra-articular implantable mechanical energy absorbing systems.

BACKGROUND

Joint replacement is one of the most common and successful operations in modern orthopaedic surgery. It consists of replacing painful, arthritic, worn or diseased parts of a joint with artificial surfaces shaped in such a way as to allow joint movement. Osteoarthritis is a common diagnosis leading to joint replacement. Such procedures are a last resort treatment as they are highly invasive and require substantial periods of recovery. Total joint replacement, also known as total joint arthroplasty, is a procedure in which all articular surfaces at a joint are replaced. This contrasts with hemiarthroplasty (half arthroplasty) in which only one bone's articular surface at a joint is replaced and unincompartmental arthroplasty in which the articular surfaces of only one of multiple compartments at a joint (such as the surfaces of the thigh and shin bones on just the inner side or just the outer side at the knee) are replaced. Arthroplasty as a general term, is an orthopaedic procedure which surgically alters the natural joint in some way. This includes procedures in which the arthritic or dysfunctional joint surface is replaced with something else, procedures which are undertaken to reshape or realigning the joint by osteotomy or some other procedure. As with joint replacement, these other arthroplasty procedures are also characterized by relatively long recovery times and their highly invasive procedures. A previously popular form of arthroplasty was interpositional arthroplasty in which the joint was surgically altered by insertion of some other tissue like skin, muscle or tendon within the articular space to keep inflammatory surfaces apart. Another previously done arthroplasty was excisional arthroplasty in which articular surfaces were removed leaving scar tissue to fill in the gap. Among other types of arthroplasty are resection(al) arthroplasty, resurfacing arthroplasty, mold arthroplasty, cup arthroplasty, silicone replacement arthroplasty, and osteotomy to affect joint alignment or restore or modify joint congruity. When it is successful, arthroplasty results in new joint surfaces which serve the same function in the joint as did the surfaces that were removed. Any chodrocytes (cells that control the creation and maintenance of articular joint surfaces), however, are either removed as part of the arthroplasty, or left to contend with the resulting joint anatomy. Because of this, none of these currently available therapies are chondro-protective.

A widely-applied type of osteotomy is one in which bones are surgically cut to improve alignment. A misalignment due to injury or disease in a joint relative to the direction of load can result in an imbalance of forces and pain in the affected joint. The goal of osteotomy is to surgically re-align the bones at a joint and thereby relieve pain by equalizing forces across the joint. This can also increase the lifespan of the joint. When addressing osteoarthritis in the knee joint, this procedure involves surgical re-alignment of the joint by cutting and reattaching part of one of the bones at the knee to change the joint alignment, and this procedure is often used in younger, more active or heavier patients. Most often, high tibial osteotomy (HTO) (the surgical re-alignment of the upper end of the shin bone (tibia) to address knee malalignment) is the osteotomy procedure done to address osteoarthritis and it often results in a decrease in pain and improved function. However, HTO does not address ligamentous instability—only mechanical alignment. HTO is associated with good early results, but results deteriorate over time.

Other approaches to treating osteoarthritis involve an analysis of loads which exist at a joint. Both cartilage and bone are living tissues that respond and adapt to the loads they experience. Within a nominal range of loading, bone and cartilage remain healthy and viable. If the load falls below the nominal range for extended periods of time, bone and cartilage can become softer and weaker (atrophy). If the load rises above the nominal level for extended periods of time, bone can become stiffer and stronger (hypertrophy). Finally, if the load rises too high, then abrupt failure of bone, cartilage and other tissues can result. Accordingly, it has been concluded that the treatment of osteoarthritis and other bone and cartilage conditions is severely hampered when a surgeon is not able to precisely control and prescribe the levels of joint load. Furthermore, bone healing research has shown that some mechanical stimulation can enhance the healing response and it is likely that the optimum regime for a cartilage/bone graft or construct will involve different levels of load over time, e.g. during a particular treatment schedule. Thus, there is a need for devices which facilitate the control of load on a joint undergoing treatment or therapy, to thereby enable use of the joint within a healthy loading zone.

Certain other approaches to treating osteoarthritis contemplate external devices such as braces or fixators which attempt to control the motion of the bones at a joint or apply cross-loads at a joint to shift load from one side of the joint to the other. A number of these approaches have had some success in alleviating pain but have ultimately been unsuccessful due to lack of patient compliance or the inability of the devices to facilitate and support the natural motion and function of the diseased joint. The loads acting at any given joint and the motions of the bones at that joint are unique to the body that the joint is a part of. For this reason, any proposed treatment based on those loads and motions must account for this variability to be universally successful. The mechanical approaches to treating osteoarthritis have not taken this into account and have consequently had limited success.

Prior approaches to treating osteoarthritis have also failed to account for all of the basic functions of the various structures of a joint in combination with its unique movement. In addition to addressing the loads and motions at a joint, an ultimately successful approach must also acknowledge the dampening and energy absorption functions of the anatomy, and be implantable via a minimally invasive technique. Prior devices designed to reduce the load transferred by the natural joint typically incorporate relatively rigid constructs that are incompressible. Mechanical energy (E) is the action of a force (F) through a distance (s) (i.e., $E=F^x s$). Device constructs which are relatively rigid do not allow substantial energy storage as the forces acting on them do not produce substantial deformations—do not act through substantial distances—within them. For these relatively rigid constructs, energy is transferred rather than stored or absorbed relative to a joint. By contrast, the natural joint is a construct comprised of elements of different compliance characteristics such as bone, cartilage, synovial fluid, muscles, tendons, ligaments, etc. as described above. These dynamic elements include relatively compliant ones (ligaments, tendons, fluid, cartilage) which allow for substantial energy absorption and storage, and relatively stiffer ones (bone) that allow for efficient energy transfer. The cartilage in a joint compresses under applied force and the resultant force displacement product represents the energy absorbed by cartilage. The fluid content of cartilage also acts to stiffen its response to load applied quickly and dampen its response to loads applied slowly. In this way, cartilage acts to absorb and store, as well as to dissipate energy.

With the foregoing applications in mind, it has been found to be necessary to develop effective structure for mounting to body anatomy. Such structure should conform to body anatomy and cooperate with body anatomy to achieve desired load reduction, energy absorption, energy storage, and energy transfer. The structure should also provide a base for attachment of complementary structure across articulating joints.

For these implant structures to function optimally, they must not cause a disturbance to apposing tissue in the body, nor should their function be affected by anatomical tissue and structures impinging on them. Moreover, there is a need to reliably and durably transfer loads across members defining a joint. Such transfer can only be accomplished where the base structure is securely affixed to anatomy. Therefore, what is needed is an approach which addresses both joint movement and varying loads as well as complements underlying anatomy and provides an effective base for connecting an implantable extra-articular assembly.

SUMMARY

Briefly, and in general terms, the disclosure is directed to base components that are mountable to a bone and may be used for cooperation with an implantable extra-articular system. In one approach, the base components facilitate mounting an extra-articular implantable link or mechanical energy absorbing system.

According to one embodiment, the base components of the link or energy absorbing system are contoured to the bone surfaces of the femur and tibia and are secured with bone screws on the medial cortices of the femur and the tibia. The bases can also be attached to lateral sides of the bones of a knee joint or on either side of members defining other joints. The base components are also designed to preserve the articulating joint and capsular structures of the knee. Accordingly, various knee procedures, including unicompartmental and total joint replacement, may be subsequently performed without requiring removal of the base components.

In one specific embodiment, the base component includes a body having an inner surface that is contoured to mate with a bone surface. The inner surface contacts the bone surface and may be porous, roughened or etched to promote osteointegration. The inner surface can be coated with an osteointegration composition. Optionally, or additionally, the base component is secured to a bone surface with a plurality of fastening members. The base component is also shaped to avoid and preserve structures of the knee. Moreover, the base component is configured to locate a mounting member on the bone in order to position a kinematic load absorber for optimal reduction of forces on a joint. The base component is a rigid structure that may be made from titanium, cobalt chrome, or polyetheretherketones (PEEK). In an alternate approach, the base can be formed at least partially from flexible material.

It is contemplated that the base component includes a low-profile body having an elongate, straight portion at a first end portion and a curved body portion at a second end portion. The second end portion is elevated as compared to the first end portion and occupies a plane displaced from the first end. An inner surface of the low-profile body has a raised portion extending along the elongate, straight portion of the body. The base component also includes a plurality of openings positioned along the elongate portion of the body. Additionally, the body can include two openings positioned side-by-side on the curved portion thereof.

According to another embodiment, the base component is a generally curved body having a first end, a second end, an outer surface, and an inner surface. The curved body is non-planar such that the second end of the body is elevated as compared to the first end of the body. In an application relating to treating a knee joint, the inner surface of the body includes a raised portion that is contoured to the medial surface of the femur above the medial epicondyle. The body also includes a plurality of openings, wherein two openings are positioned side-by-side near the second end. Additionally, the openings provide differing trajectories for receiving fastening members.

In one particular approach, the disclosed base has an osteointegration surface area greater than 39 mm². More specifically, a femoral base component can embody a surface area of 971 mm² and a tibial component can have a surface area of approximately 886 mm². The bases can further be coated with a titanium plasma spray having a thickness of 0.033 inches plus or minus 0.005 inches. Alternatively, an hydroxyapatite plasma spray resulting in a 35 μm plus or minus 10 μm thickness is contemplated.

Moreover, it is contemplated that various sized bases be made available. In that regard, due to expected variability in anatomy, up to five or more femoral base sizes and two or more tibial base sizes can be available to a physician.

The bases can be configured so that relative motion between a base component and a mating bone is less than 150 microns. For certain applications, the durability of the base to bone connection as well as material should be such that the structure can withstand five million cycles of functional loading.

Other features and advantages will become apparent from the following detailed description, taken in conjunction with the accompanying drawings, which illustrate by way of example, the features of the various embodiments.

BRIEF DESCRIPTION OF THE DRAWINGS

FIG. 10A is a side view of another embodiment of an inner surface of the base component for mounting to a bone.

FIG. 10B is a perspective view of yet another embodiment of inner surface of the base component.

FIG. 11 is a side view of one embodiment of a base component fixed to a femur.

DETAILED DESCRIPTION

Figure 1A:
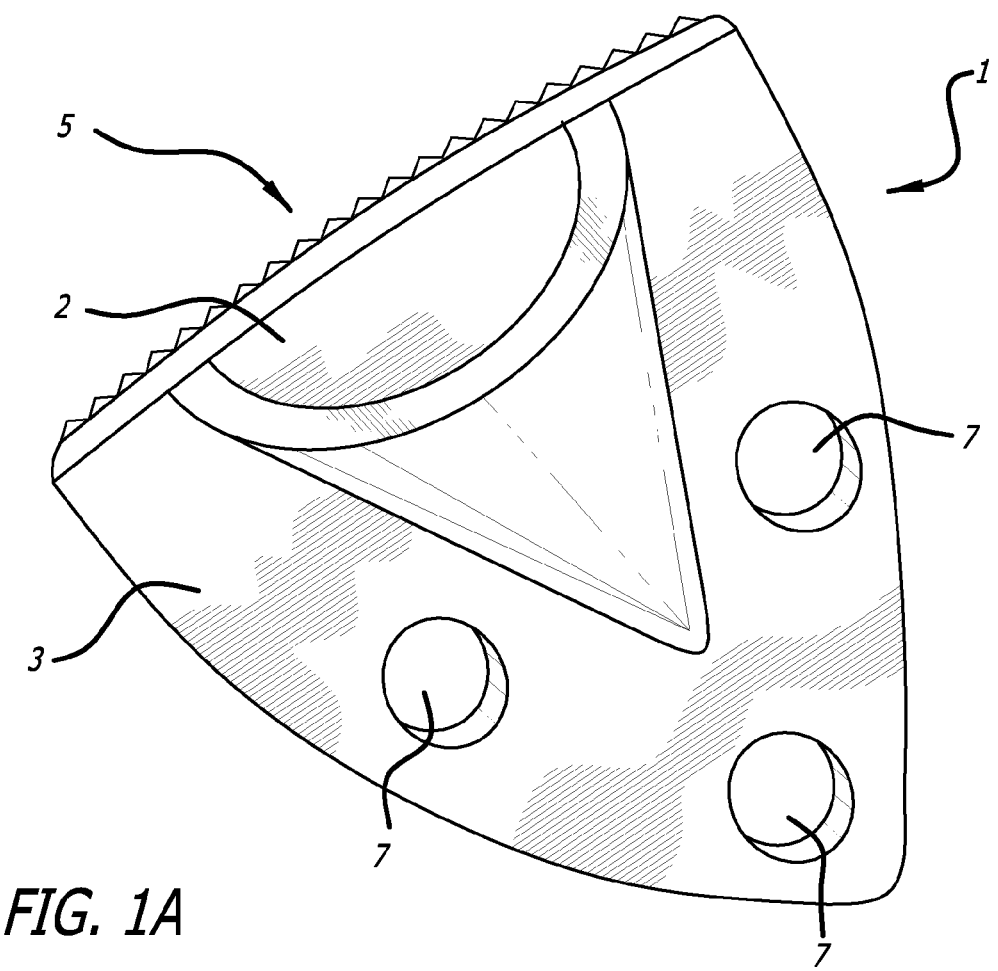
FIG. 1A is a perspective view of one embodiment of a base component.

Various embodiments are disclosed which are directed to base components for attachment to body anatomy. In a preferred approach, femoral and tibial base components are provided for attachment to extra-articular implantable link or mechanical energy absorbing systems.

In a specific embodiment, the femoral and tibial base components are contoured to the medial surfaces of the femur and tibia, respectively. The base components have a low-profile design and contoured surfaces thereby minimizing the profile of the base components when mounted to the bone surface and enabling atraumatic soft tissue motions over the bone components. The base component is secured to a bone surface with one or more fastening members. Optionally, or additionally, the inner surface of the base components may be modified to promote osteointegration of the base component into bone. Osteointegration is a process of bone growth onto and about an implanted device that results in integrating the implant to the bone, thereby facilitating the transfer of load and stress from the implant directly to the bone. After osteointegration, fasteners used to initially attach the base component to bone no longer are needed to carry the load and stress from the implant.

The base component can be configured to be an anchor for the extra-articular implantable link or mechanical energy absorbing system used to reduce forces on the knee or other joints (e.g., finger, toe, elbow). The base component can be also designed to distribute loads onto the bone from an extra-articular implantable link or mechanical energy absorbing system while avoiding articulating joint and capsular structures.

Various shapes of bases are contemplated and described. Moreover, it is contemplated that various sized and similar shaped bases be made available to a physician so that a proper fit to variably sized and shaped bones can be accomplished. In that regard, it is contemplated that up to five or more different femoral bases and two or more different tibial bases can be available to a physician.

The base components disclosed herein are structures that are different and distinct from bone plates. As defined by the American Academy of Orthopedic Surgeons, bone plates are internal splints that hold fractured ends of bone together. In contrast, the base components disclosed herein are designed to couple to and transfer loads from a link of an implanted extra-articular system to the bones of the joint. Furthermore, the loading conditions of a bone plate system are directly proportional to the physiological loads of the bone it is attached to, by contrast the loading conditions of a base is not directly proportional to the physiological loading conditions of the bone but is directly proportional to the loading conditions of the link to which it is coupled. In various embodiments, the base component is configured to transfer the load through a combination of the fastening members used to secure the base component to the bone and/or one or more osteointegration areas on the base component.

Further, previous approaches and studies on osteointegration surfaces have not considered cyclic loading. Thus, the approaches to the bases disclosed herein address needs in this area and in particular, provides an approach which achieves extra-cortical boney in-growth under cyclic loading. In certain disclosed applications, a shear strength of about 3 MPa or more can be expected.

Referring now to the drawings, wherein like reference numerals denote like or corresponding parts throughout the drawings and, more particularly to FIGS. 1-20B, there are shown various embodiments of a base component that may be fixed to a bone. In one specific application, the base components are configured to be affixed to members defining a joint. Moreover, in one particularly specific approach, the base can be configured to include a surface contacting periosteum.

Figure 1B:
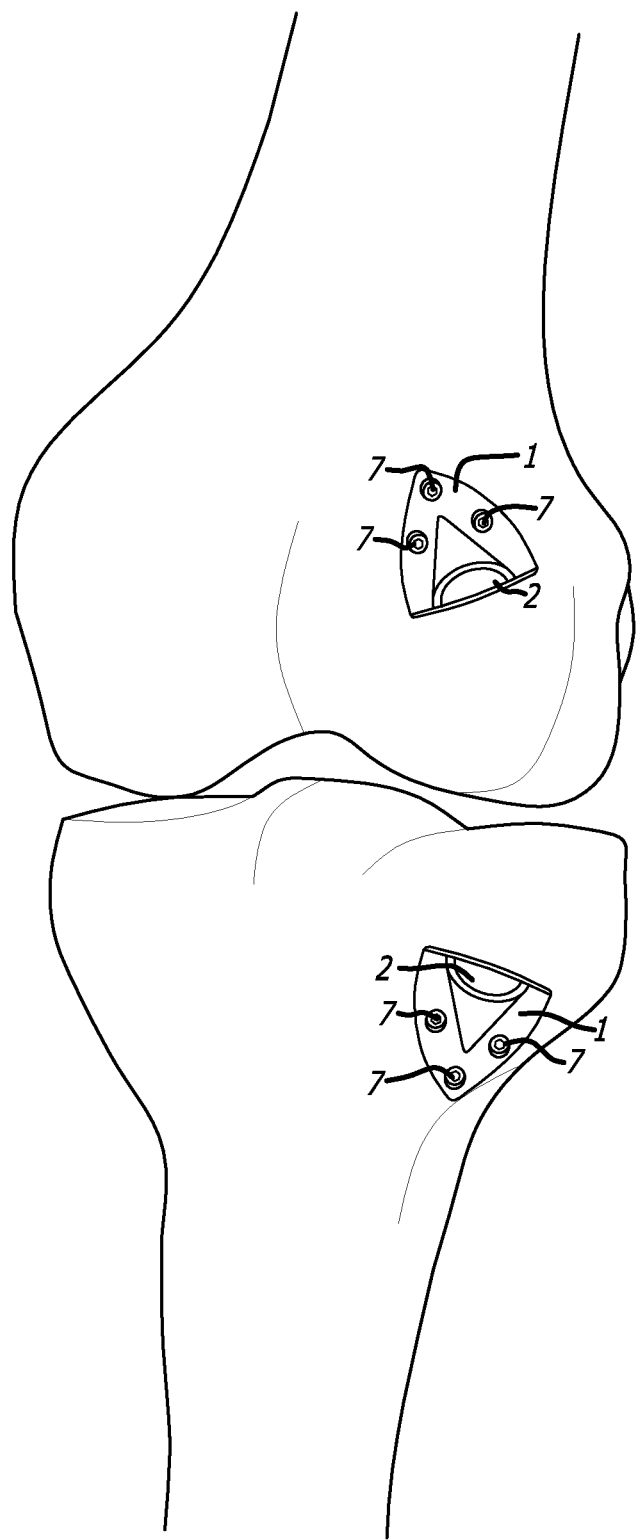
FIG. 1B is a perspective view of the base component of FIG. 1A mounted to a bone.
Figure 2:
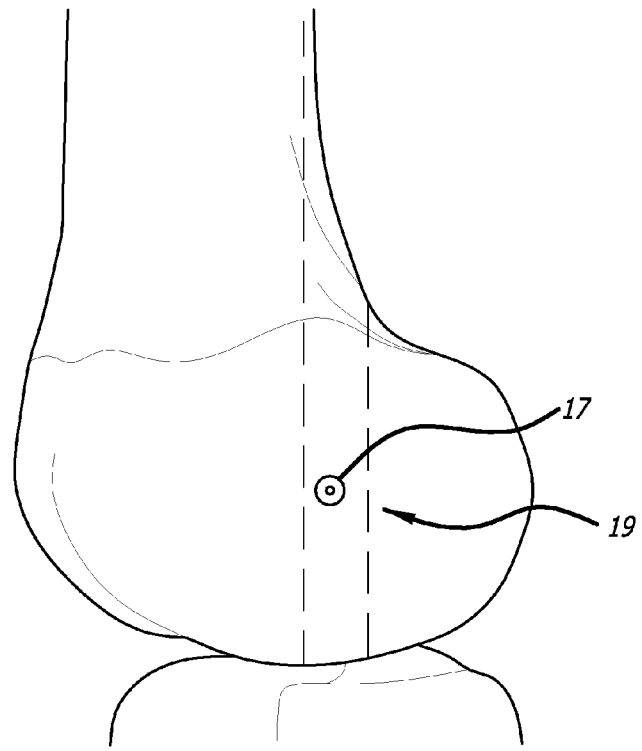
FIG. 2 is side view of a femur and indicates a preferred location of a pivot point for an extra-articular mechanical energy absorbing system.

Turning now to FIGS. 1A-1B, a base component 1 fixable to the medial surface of a femur is illustrated. It is to be recognized, however, that the base component 1 can be configured to be fixed to a lateral side of the femur, on the tibia, or other anatomy of the body. The base component 1 includes an outer surface 3 and an inner surface 5. The outer surface 3 of the base component has a low-profile and is curved to eliminate any edges or surfaces that may damage surrounding tissue when the base component is affixed to bone. The base component 1 includes a locking hole 2 that locates a coupling structure 15 adjacent point 17 (FIG. 2). The femoral base component 1 is intended to be positioned about the center 19 of knee rotation in FIG. 2. According to one embodiment, the base component 1 is mounted to the femur so that the coupling structure 15 is located approximately 6 mm anterior and approximately 1 mm superior to the center 19 of rotation of the knee on the medial epicondyle. Such spacing is relevant to each of the disclosed embodiments. Mounting the energy absorbing components at this location allows the extra-articular mechanical energy absorbing system to reduce forces during the heal strike to toe-off phase of a person's gait. Alternatively, the base component may be mounted at different positions on the femur to reduce forces during different phases of a person's gait.

Figure 1C:
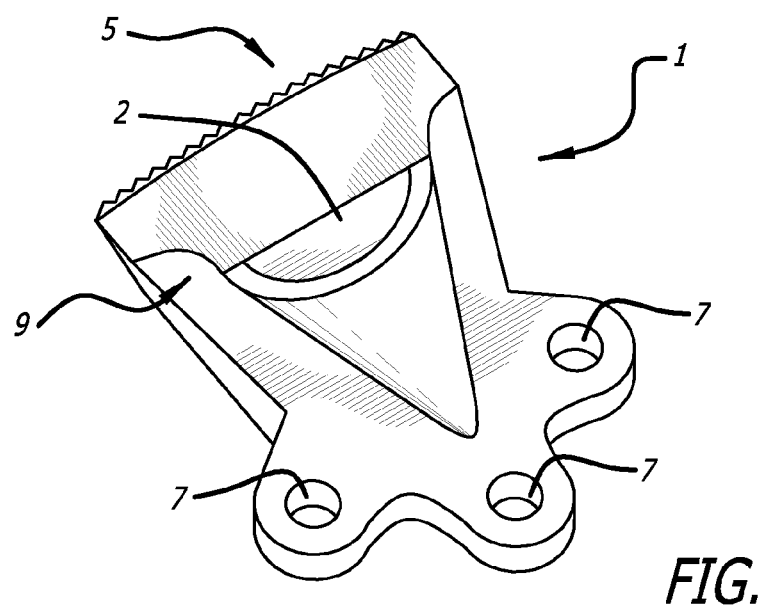
FIG. 1C is a perspective view of another embodiment of a base component.
Figure 1D:
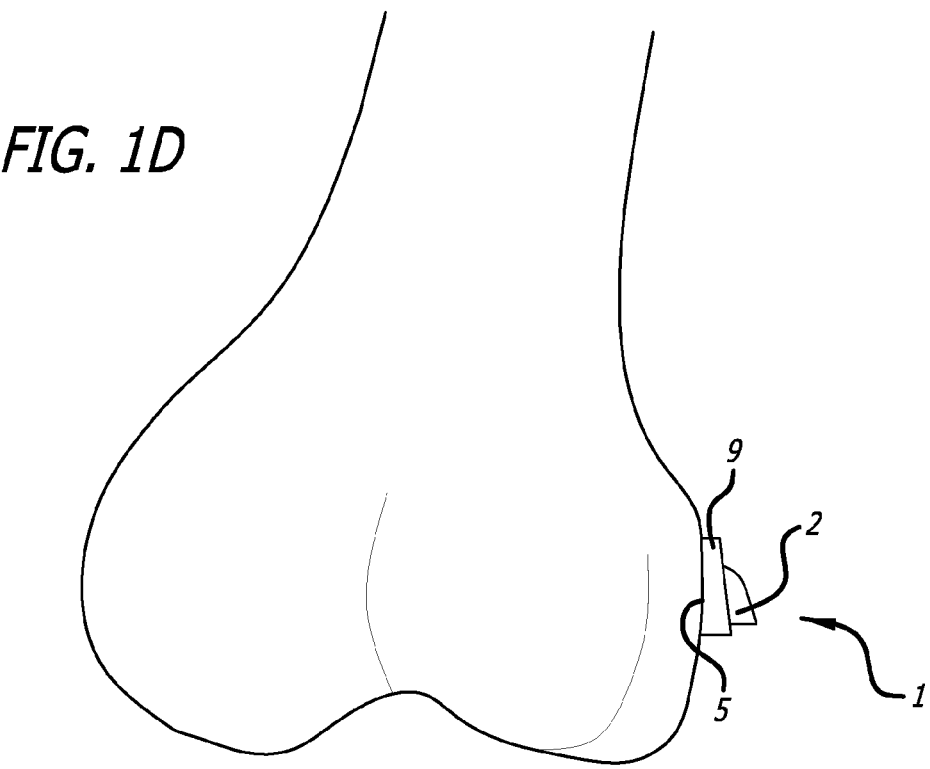
FIG. 1D is a side view depicting the base component of FIG. 1C mounted to a bone.

FIGS. 1C-D illustrate another embodiment of a base component 1 mountable on the medial surface of the femur. Again, it is noted that this embodiment of the base component 1 can be positioned laterally as well as on other anatomy. The base component 1 includes a raised surface 9 to suspend the taper locking opening 2 higher off the bone surface to avoid the knee capsule and associated structures of the knee joint. It is contemplated that the taper locking opening 2 be offset approximately 10 mm or less from the surface of the joint capsule. In one specific embodiment, the taper locking opening 2 is offset approximately 3 mm from the capsular structure. In another approach, the taper locking opening 2 is offset approximately 6 mm from the capsular structure. Accordingly, the base component 1 allows for positioning of an extra-articular device on the knee joint while preserving the knee for procedures such as ACL or PCL repair or replacement, Pes replacement, or total knee replacement.

It is contemplated that the inner surface of the base component 1 be contoured to directly contact the bone surface. The inner surface may be curved in an anterior to posterior direction as well as superior to inferior directions.

According to one embodiment, the inner surface includes one or more compositions that induce osteointegration to the cortex of long bones in the body. The inner surface represents the base component 1 to bone surface area required to support expected shear forces resulting from 40 lbs. of load carrying. Alternatively, the inner surface 5 is roughened or etched to improve osteointegration.

The surface area of the osteointegration area is proportional to the forces being carried at a joint by the extra-articular mechanical energy absorbing system. For example, the surface area of the inner surface is at least 39 mm$^2$ for a secure fixation to the femur and in order to carry 40 pounds in 4 mm of compression of a kinematic load absorber. A safety factor may be built into base component as larger surfaces may be used in other embodiments. For example, a femoral base component can include an osteointegration surface area of approximately 971 mm$^2$. Alternatively, a tibial base component includes an osteointegration surface area of approximately 886 mm$^2$.

In certain embodiments, the load transferred from the absorber to the base component can change over time. For example, when the base component is initially fixed to the bone, the fastening members carry all the load. Over time, as the base component osteointegrates with the underlying bone, both the fastening members and the osteointegrated surface carry the load from the implanted system. Once the base component is completely osteointegrated with the underlying bone, the osteointegration area carries most (if not all) the load. Due to the same, the energy absorbing system may be configured in an inactive state, only later activating the device once sufficient osteointegration has occurred.

Alternatively, the implant may be intended for temporary use and so removability of the components is important. In these instances boney in-growth is not desirable. To prevent boney in-growth no porous coating is applied and alternative surface geometry and/or material may be used that does not encourage bone growth, additionally the fasteners are designed to carry 100% of link loads for duration of implantation.

The base component also includes a plurality of openings 7 that are sized to receive fastening members used to permanently secure the base component to the bone. The openings 7 define through-holes that may receive fastening members such as compression screws and/or locking screws. As shown in FIGS. 1A-D, the openings 7 are spaced about the outer surface 3 of the base component 1. In one embodiment, the openings can be positioned on the outer surface 3 such that they are located as close as possible to the taper locking opening 2. The openings 7 may also have divergent bore trajectories to further maximize the pull forces required to remove the base component from the bone. The number and trajectories of the openings may be varied in alternate embodiments.

Figure 3:
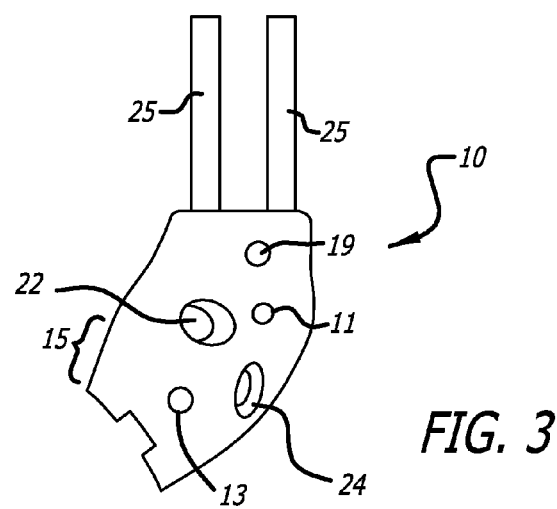
FIG. 3 is a side view of another embodiment of a base component for mounting to a bone.
Figure 4:
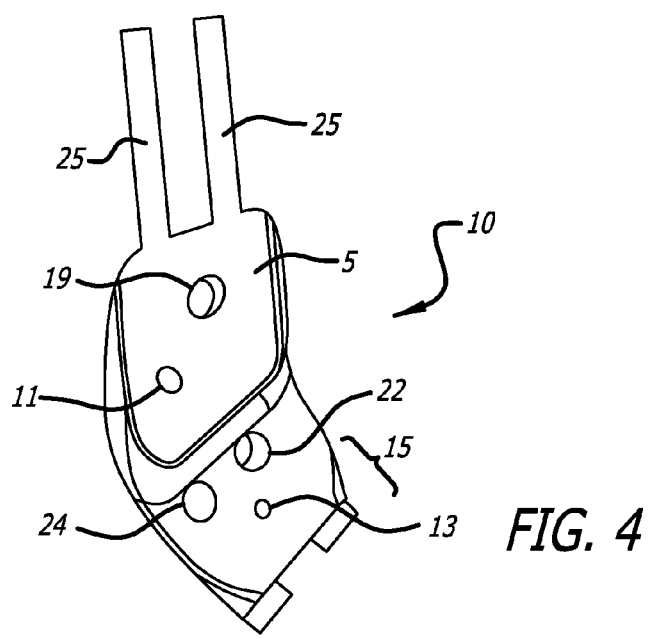
FIG. 4 is view of an inner surface of the base component shown in FIG. 3.
Figure 5:
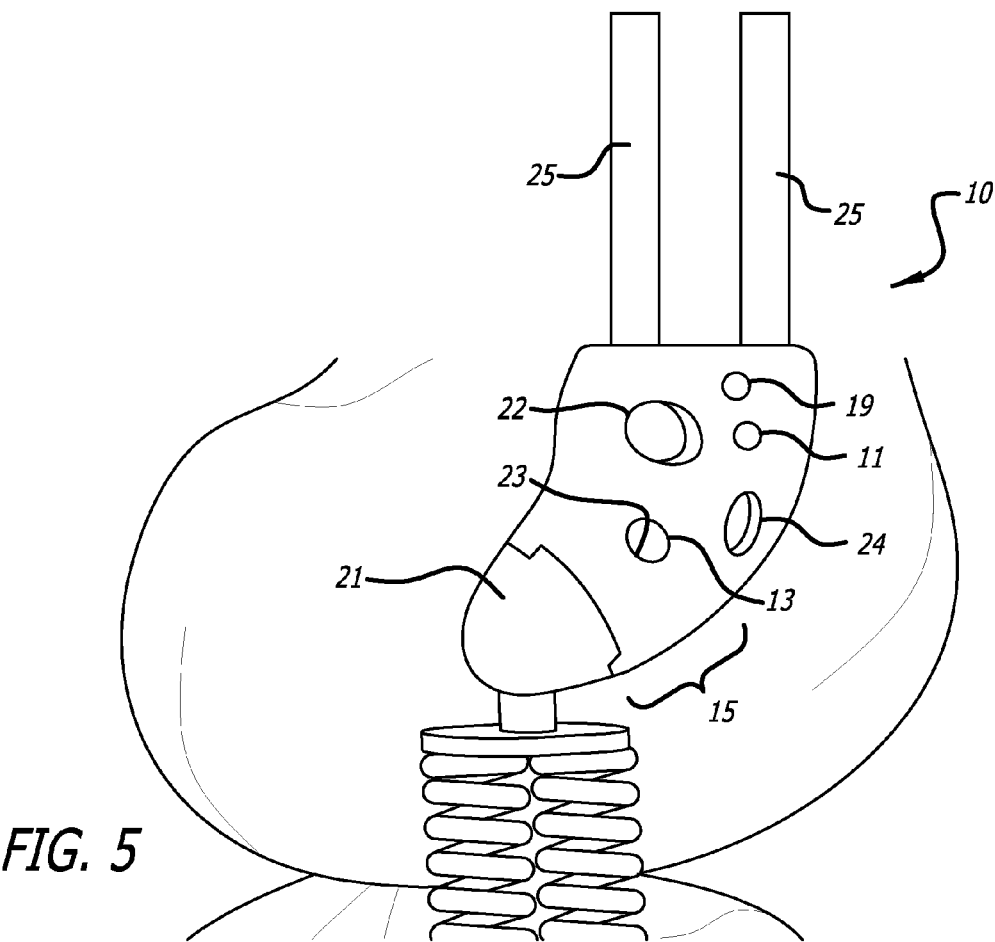
FIG. 5 is a side view of the base component shown in FIG. 3 mounted on a bone.

FIGS. 3-4 illustrate another embodiment of a base component 10. The base component includes a body that is configured to position a mounting member (not shown) at a point 17 superior and anterior to the center 19 of knee rotation on the medial epicondyle as shown in FIG. 2. The base component 10 also includes osteointegration rods 25 that extend along the surface of the bone. It is contemplated that the osteointegration rods 25 follow the contours of the bone surface. Accordingly, the osteointegration rods 25 can be made of malleable materials. In another embodiment, osteointegration rods 25 can be configures to penetrate the bone surface as shown in FIGS. 3-4. The osteointegration rods 25 have a sufficient surface area to allow for the transfer of the forces of the implanted system onto the bone. According to one embodiment, all of the surfaces of the osteointegration rods 25 include materials or is treated to promote bone growth.

As shown in FIGS. 3-4, the base component 10 includes a plurality of openings 11, 19, 22, 24. Opening 11 has a diameter sized to receive standard K-wires that are used to temporarily locate the base component 10 on the bone. Openings 19, 22, 24 are sized to receive fastening members used to permanently secure the base component to the bone. Openings 19 define through holes for compression screws and opening 22, 24 are configured to receive locking screws. In one embodiment, the locking screw openings 22, 24 are threaded. As shown in FIGS. 3-4, the openings 22, 24 are located near the mounting end 15 of the base component in order to receive fasteners which securely fix the base component to the bone and maximize pull-out forces. The openings 22, 24 may also have divergent bores trajectories to further maximize the pull forces required to remove the base component from the bone. The number and trajectories of the openings may be varied in alternate embodiments. A post access port 13 is provided near the mounting end 15 of the base component 10 (see for example FIG. 5). The post access port 13 is sized to receive a tool that allows for disassembly of a mount member (not shown) from the base component 10 by pushing the post 23 of the mount member out of the base component. Openings 26 additionally alter the stress distribution on cortical bone surface that can stimulate boney remodelling. Bone can grow up into these holes further adding shear strength to the bone implant interface.

Figure 6:
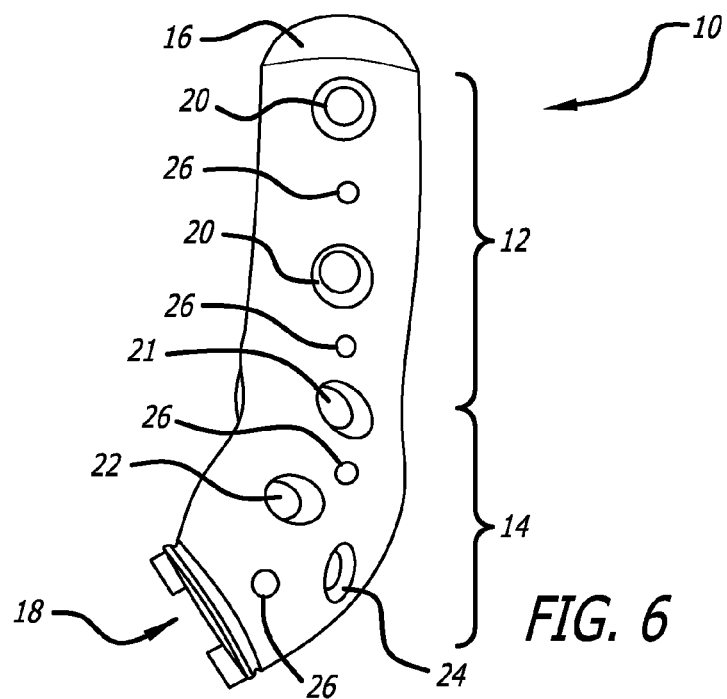
FIG. 6 is a side view of an alternate embodiment of a base component for mounting to a bone.

Turning now to FIG. 6, a presently preferred embodiment of a base component 10 that is mountable to a femur is shown. The base component 10 includes a body having an elongated portion 12 and a curved portion 14. The body is generally narrow having a rounded first end 16 and a squared-off second end 18. In various embodiments, the second end 18 is configured to attach to mounts and/or devices for absorbing energy at a joint. As shown in FIG. 6, the upper surface of the body is a generally curved such that a center of the body is thicker than the edges of the body. The base component 10 also includes rounded edges in order to minimize sharp edges that may otherwise cause damage to surrounding tissues when the component is coupled to body anatomy such as the femur.

Figure 7:
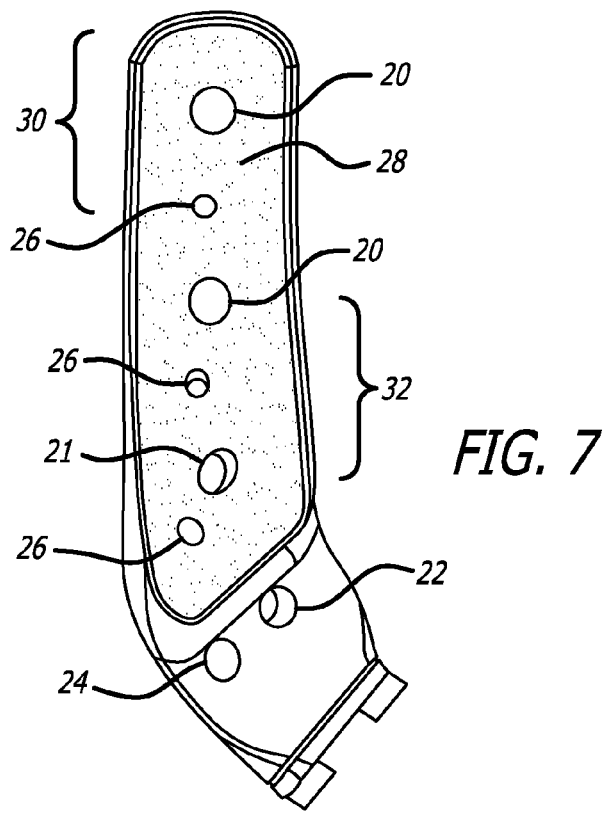
FIG. 7 is a side view of an inner surface of the base component shown in FIG. 6.

As shown in FIG. 7, the body also includes a plurality of openings 20 and 21 configured to receive fastening members. The openings 20 and 21 are generally aligned along the center of the elongate portion of the body. The openings 20 and 21 on the elongated portion of the body 12 are positioned such that the fastening members contact the osteointegration area of the femur. According to one embodiment, the openings 20 and 21 are configured to accept compression screws that compress the base component 10 onto the bone surface. The compression screws may be cancellous screws of either uni-cortical or bicortical design. The openings 20 are sized to accommodate a particular screw size.

Figure 12:
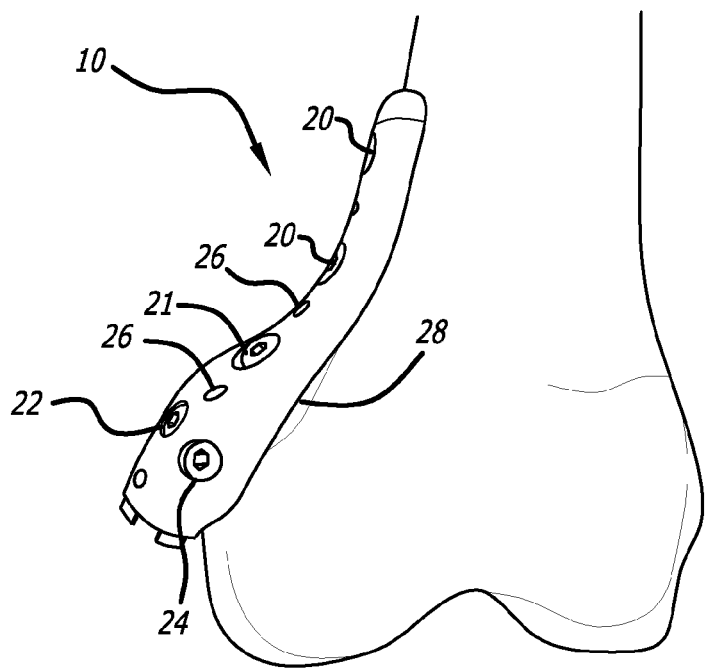
FIG. 12 is a front view of one embodiment of a base component fixed to the medial surface of a femur.

Additionally, two openings 22, 24 are provided on the curved portion 14 of the body. The openings 22, 24 are positioned such that fastening members inserted there through (as shown in FIGS. 11-12) will be configured closer to the center of rotation of the femur. In one embodiment, the fastening members 22, 24 are locking screws and the openings 22, 24 include threads for engaging like structure of the locking screws. It is to be recognized that locking screws securely anchor the base to the bone such that the relative motion between the base component 10 and the mating bone is less than 150 microns. The locking screws function to stabilize the base component as micro-motions of the base component prevent osteointegration of the base component.

Additionally, the openings 20, 21, 22, 24 can be oriented to provide fastening member trajectories that maximize pull out forces thereby minimizing the possibility that the base component is separated from the bone. According to one embodiment, the trajectories of the openings are oriented such that the opening trajectories are normal or approximately normal to the shear loading forces on the base component 10. For example, the two openings 22, 24 on the curved portion 14 of the body have differing fastening member trajectories as the posterior opening 22 orients a fastening member at a downward trajectory (See FIG. 18), and the anterior opening 24 orients a fastening member at an upward trajectory (See FIG. 19).

The openings 20, 21, 22, 24 can be countersunk to allow the fastening members to sit below the surface of the base body as shown in FIG. 10. In one specific approach, the openings 20 are sized to accommodate 4.0 mm screws. In other approaches, the openings 20 may be sized to accommodate 3.5 mm, 4.5 mm, 5.0 mm, or 6.5 screws.

In a preferred embodiment, two openings 20 on the elongated portion of the base component 10 are sized and threaded to accommodate 3.5 mm bicortical compression screws. The most inferior opening 21 on the elongated portion of the base component is sized to accommodate a 6.5 mm unicortical compression screw. The openings 22, 24 on the curved portion 14 of the body are sized and threaded to accommodate 4.5 mm locking screws.

While screws are used to fix the base component 10 to the bone, those skilled in the art will appreciate that any fastening members known or previously developed may be used to secure a base component to a bone. For example, in other embodiments, a fastening device similar to a moly bolt or a toggle bolt is used to secure the base component to a bone. Additionally, FIGS. 1-11 illustrate a base component 10 having five fastener openings 20, 21, 22, 24; however, it is contemplated that other embodiments of the base component may be have any number of openings having various screw trajectories.

Referring back to FIG. 6, the base component 10 also includes a plurality of holes 26 that may be used for aligning the base component on the bone. Optionally, the base component 10 may include a plurality of holes (not shown) to promote bone in-growth thereby improving base component stability. In this regard, K-wires can be configured through the holes 26 to maintain alignment of a base to bone during its affixation thereto by fastening members.

FIG. 7 illustrates a view of the inner surface 28 of the base component 10. As shown, the inner surface 28 is a roughened or etched surface to improve osteointegration. Alternatively, the inner surface 28 is modified to induce bone growth. Thus, osteointegration can be obtained through mechanical interlocking or as a result of chemical loading. For example, the inner surface 28 may be coated with bone morphogenic protein 2 (BMP-2), hydroxyapatite (HA), titanium, cobalt chrome beads, or any other osteo-generating substance. According to one embodiment, a titanium plasma spray having a thickness of approximately 0.033 in.±0.005 in. is applied to the inner surface 28. In another embodiment, a HA plasma spray having a thickness of approximately 35 μm±10 μm is applied to facilitate osteointegration.

As shown in FIG. 7, the inner surface 28 has a first radius of curvature at the proximal end 30 of the base component 10 and a second radius of curvature at the distal end 32 of the inner surface where the first radius of curvature is greater than the second radius of curvature. Alternatively, the first radius of curvature is less than the second radius of curvature. In another embodiment, the first and second radii of curvature are approximately equal.

Figure 8:
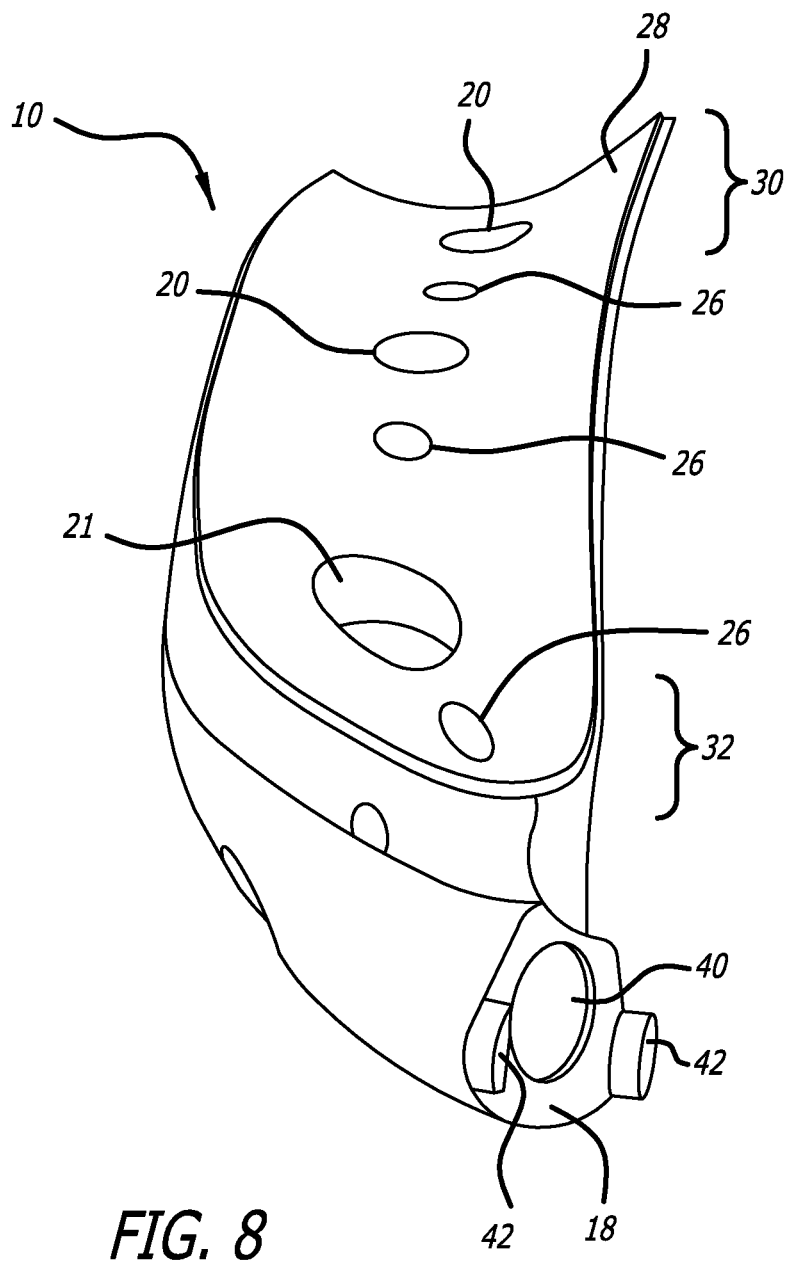
FIG. 8 is a perspective view of the inner surface of the base component shown in FIG. 6.

Additionally, as best seen in FIG. 8, the inner surface 28 is generally helical in shape when moving from the proximal end 30 of the base component 10 to the distal end 32 of the base component. That is, the inner surface 28 twists when moving from the top of the inner surface to the bottom of the inner surface. The helical nature of the inner surface 28 generally follows contours of the femur when moving distally (down the femur) and posteriorly (front to back). Accordingly, the contouring of the inner surface 28 helps to reduce the overall profile of the base component 10 when affixed to the medial surface of the femur. Additionally, the contouring of the inner surface 28 increases the surface area in which the base component contacts the femur thereby improving load distribution.

Figure 9A:
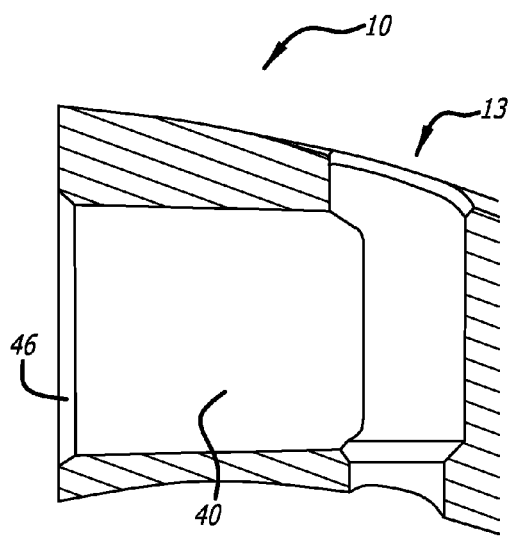
FIG. 9A is a cross-section view of the end of the base component that receives a mounting member.

Additionally, as shown in FIG. 8, the end 18 of the base component 10 includes a bore 40. The bore 40 is sized to receive a post (See FIG. 9B) of a mounting member 15. According to one embodiment, the bore 40 has a uniform inner diameter. Alternatively, the bore 40 is tapered (e.g., inner diameter decreases when moving away from the opening of the bore). In yet another embodiment, a funnelling feature 46 is provided around the opening of the bore 40 as shown in FIG. 9A. The funnelling feature 46 acts as a guide to facilitate the insertion of the mounting member into the bore. The end 18 of the base component 10 also includes alignment members 42 for properly orienting the mounting member (not shown) on the base component.

Figure 9C:
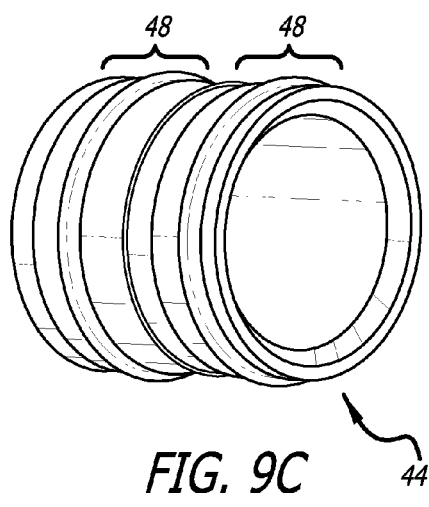
FIG. 9C is a perspective view of the sleeve shown in FIG. 9B.
Figure 9B:
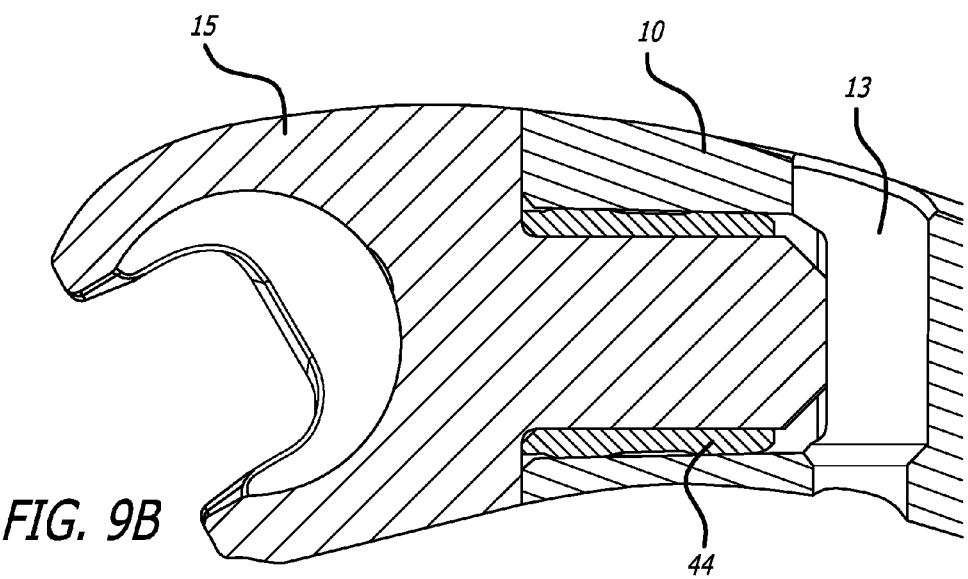
FIG. 9B is a cross-sectional view of the end of the base component shown in FIG. 3.

FIGS. 9B-C illustrate a cross-section view of one embodiment of the bore 40 of the base component 10 including a sleeve 44. The sleeve 44 acts as a sacrificial piece of material that prevents damage to the bore 40 while providing a good secure fit between the mounting member and the base component. In one embodiment, the sleeve 44 is press fit into the bore 40. The inner diameter of the sleeve 44 can be uniform or alternatively, the outer diameter is variable. Additionally, one or more rings can be provided on the outer diameter of the bore 40. As the sleeve 44 is inserted into the bore 40, the rings 48 on the outer diameter deform thereby providing a secure connection between the base component 10 and the mounting member 15. Additionally, the sleeve 44 facilitates the removal of the mounting member 15 from the base component 10. Additionally, interpositional segments can be placed at the end 18 of the bone component 10 to change the length of the base component. The two part base/mounting member system provides a method for good attachment of the base to the bone and a more simple surgical technique for installing the link assembly. It also allows a sheath (not shown) and/or wear components of the link/mounting member assembly to be removeable and/or replaceable without removing or replacing the base components. It further allows the wear components of the link/mounting member assembly and the base components to be different materials. For example, the base components can be titanium or titanium alloy which promote osteo-integration and the wear components can be much harder materials such as cobalt chrome (e.g., Biodur CCM Plus), ceramic, or other durable materials that produce a minimal amount of particulate material or, if particulate material is generated, the smallest size of particulate material.

With reference to FIG. 10A, another embodiment of the inner surface 28 of a base component is shown having a plurality of spikes 34 projecting out of the inner surface. While the spikes 34 shown in FIG. 10A are solid, it is contemplated that the spikes (not shown) may also include an inner bore (similar to a needle) that promotes for bone in-growth. According to one embodiment, the spikes 34 may be positioned anywhere on the inner surface 28 (e.g., randomly dispersed or concentrated in one or more areas) in order to preserve critical anatomy (e.g., periosteal vessels), improve pull out forces (i.e., more force required to pull component away from bone), and/or stimulate osteointegration. The spikes 34 may extend approximately 2 mm from the inner surface 28 of the base component 10. As those skilled in the art will appreciate, any useful spike length is contemplated. In yet another embodiment, one or more hollow tabs 36 are provided on the inner surface 28 as shown in FIG. 10B. The tabs 36 may be any shape (e.g., rectangular, triangular, or any polygonal shape) having a hollow opening (i.e., the walls of the tab form the perimeter of the shape) thereby promoting osteointegration and stability to the base component 10.

FIGS. 11-12 illustrate the base component 10 affixed to the medial surface of the femur. As best seen in FIG. 12, the base component 10 has a generally low-profile when mounted to the bone. The base component 10 is affixed to the medial surface of the femur in order to preserve critical anatomy such as, but not limited to, medial collateral ligaments while positioning the second end 18 of the base component as close to the center of rotation of the femur. Moreover, the curved portion 14 of the base component 10 is offset from the surface of the bone to avoid critical structure while maintaining a low profile of the device.

The base component 10 shown in FIGS. 1-12 is configured to be fixed to the medial surface of the left femur. It is to be appreciated that a mirror image of the base component 10 shown in FIGS. 1-12 would be fixable to the medial surface of the right femur. In an alternate embodiment, the base component may be configured to be fixed to the lateral surface of the left or right femur. In yet another approach, base components may be fixed to both the lateral and medial surfaces of the left or right femur.

Figure 13:
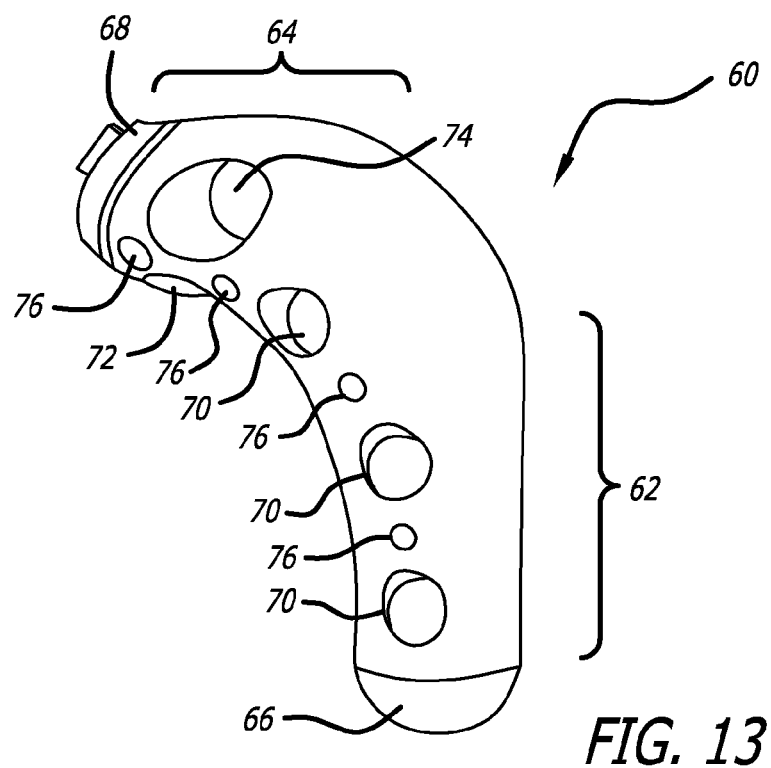
FIG. 13 is a perspective view of another embodiment of a base component for mounting to a bone.

A presently preferred embodiment of base component 60 that is mountable to the medial surface of the tibia is depicted in FIG. 13. As shown, the tibial base component 60 has an overall curved shape. The base component 60 includes a main body portion 62 and an arm portion 64. The arm portion 64 of the base component 60 is shaped to position a link or absorber assembly approximately perpendicular to the tibial plateau to provide desired alignment across the joint. Alternatively, the arm portion 64 may be angled relative to the tibial plateau in order to provide some torque across the joint. The upper surface of the body is a curved convexly where the center of the body is thicker than the edges of the body. The base component 60 also includes rounded edges in order to minimize sharp edges that may otherwise cause damage to surrounding tissues when the component is coupled to the tibia. The main body portion 62 is generally narrow and includes a rounded first end 66 and a squared-off second end 68. In various embodiments, the second end 68 is configured to attach to mounts and devices for absorbing energy at a joint. The main body portion 62 is the portion of the base component 60 that contacts the tibia. The arm portion 64 is offset laterally from the bone (i.e., the arm portion does not contact the tibia). While the arm portion 64 of the base component 60 is offset from the bone, the base component defines a low-profile when mounted to the bone.

As shown in FIGS. 13-17, the base component 60 also includes a plurality of openings 70. The openings 70 are aligned along the center portion of the base component 60.

Figure 18:
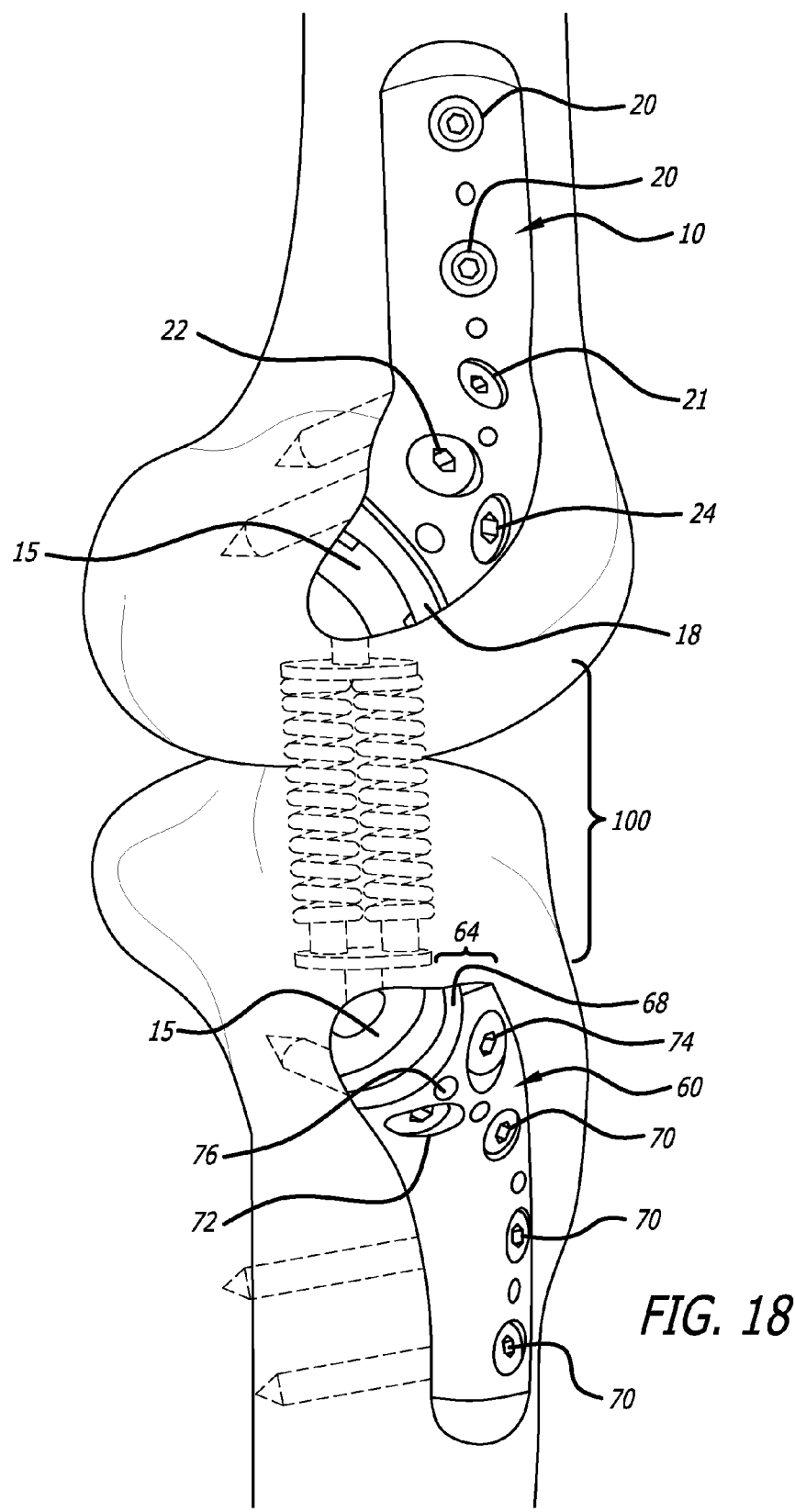
FIG. 18 is a side view of a juxtapositional relationship of the base components to one embodiment of an extra-articular implantable mechanical energy absorbing system.
Figure 19:
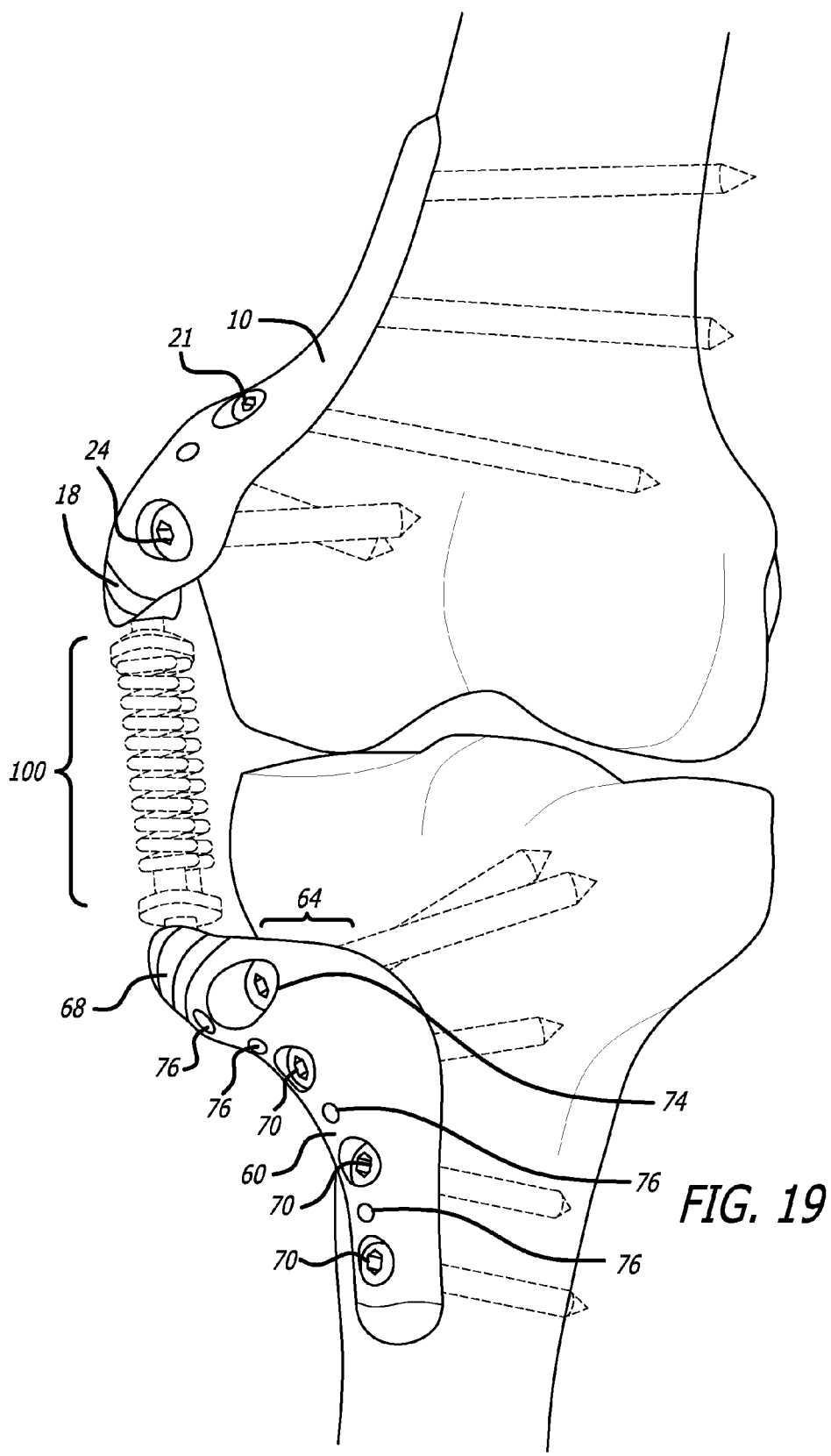
FIG. 19 is a front view of the embodiment shown in FIG. 18.

The openings 70 are positioned such that the screws contact the osteointegration area of the tibia. Additionally, two openings 72, 74 are provided on the arm portion 64 of the base component 60. The two openings 72, 74 are positioned such that the screws (as shown in FIGS. 18-19) will be mounted closer to the mounting location of the mounting member (not shown) at the end of the base component.

Additionally, the openings 70, 72, 74 are oriented to provide differing trajectories for fastening members that maximize pull forces thereby minimizing the possibility that the base component 60 is separated from the bone. According to one embodiment, the opening trajectories are oriented such that the hole trajectories are normal or approximately normal to the shear loading forces on the base component 10. For example, as shown in FIG. 19, the two openings 72, 74 on the arm portion 64 of the base component have differing trajectories, the posterior opening 72 orienting a fastening member at an upward trajectory, and the anterior opening 74 orienting a fastening member at a slightly upward trajectory.

Figure 16:
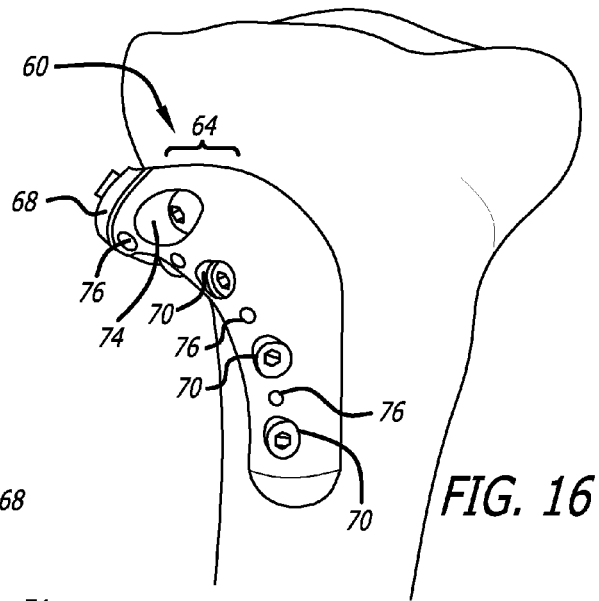
FIG. 16 is a front view of the base component of FIG. 13 mounted to the medial surface of a tibia.
Figure 17:
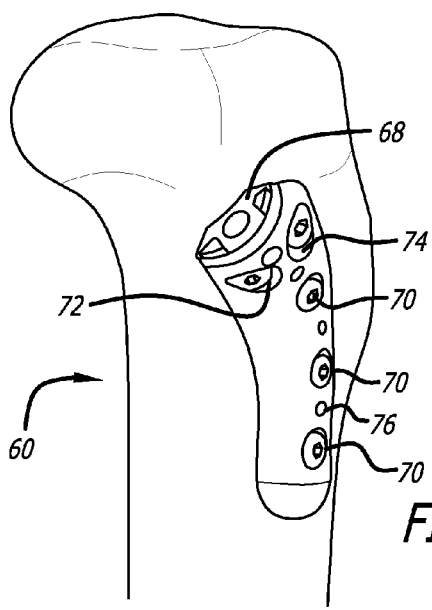
FIG. 17 is a side view of the base component of FIG. 13 mounted to the medial surface of the tibia.

The openings 70, 72, 74 can be countersunk to allow the heads of fastening members to sit below the surface of the body as shown in FIGS. 16-17. According to one embodiment, the openings 70, 72, 74 are sized to accommodate 4.0 mm diameter fastening members. In other embodiments, the openings 72, 74 may be sized to accommodate 3.5 mm, 4.5 mm, or 5.0 mm diameter fastening members. Additionally, the inner bores of the openings 70, 72, 74 may be threaded for use with locking screws (i.e., head of the screw also includes threads that engage threads in the bore of the screw hole). In preferred approaches, a combination of compression screws and locking screws are used to secure the base component 60 to a bone.

While screws are used to fix the femoral and tibial base components 10, 60 to the bone, those skilled in the art will appreciate that any fastening members known or developed in the art may be used to accomplish desired affixation. Although the base components 10, 60 depicted in FIGS. 6-7 and 13-14 illustrate structure having five openings, it is contemplated that other embodiments of the base component may be have any number of openings. Additionally, the openings may be oriented such that fastening members will have different trajectories.

As shown in FIG. 13-17, the tibial base component 60 also includes a plurality of holes 76 that may be used during alignment of the base component 60 on the tibia and sized to receive structure such as a K-wire. Optionally, the base component 60 may include a plurality of holes (not shown) to promote bone in-growth thereby improving base component stability.

Figure 14:
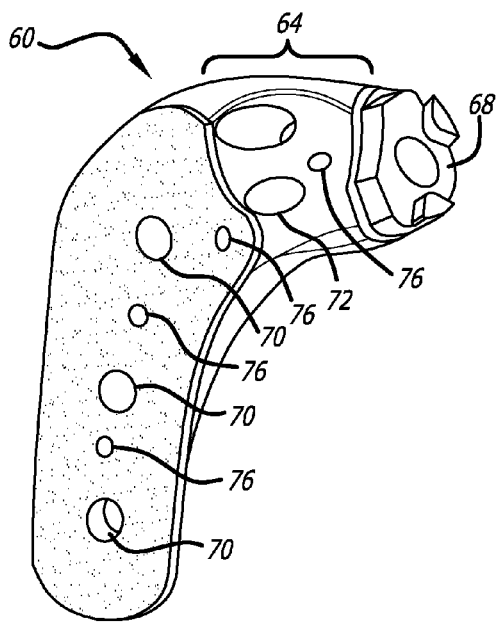
FIG. 14 is a perspective view of an inner surface of the base component shown in FIG. 13.
Figure 15A:
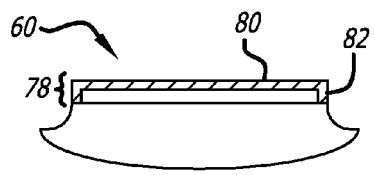
FIG. 15A is a cross-section view of one embodiment of the base component shown in FIG. 14.
Figure 15B:
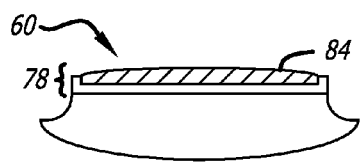
FIG. 15B is a cross-section view of one embodiment of a portion of the base component shown in FIG. 14.

FIG. 14 illustrates a perspective view of the inner surface 78 of the tibial base component 60. The inner surface 78 represents the base to bone surface arch required to support expected shear forces resulting from 60 lbs. of load carrying. As shown in FIG. 14, the inner surface 78 is a roughened surface for improving osteointegration. Alternatively or additionally, the inner surface 78 is coated to induce bone growth. For example, the inner surface 78 may be coated with bone morphogenic protein 2 (BMP-2) or hydroxyapatite, titanium, cobalt chrome beads. As shown in FIGS. 15A-15B, the inner surface 78 is a contoured surface that promotes good contact between the base component 60 and the tibia. Accordingly, the inner surface facilitates the base component 60 absorbing and transferring load forces from the base component to the tibia. Similar to the embodiments disclosed in FIGS. 10A-10B, the inner surface 78 of the base component 60 may include one or more spikes or tabs.

FIGS. 15A-B are cross-sectional views of the inner surface 78 of the tibial base component 60. As shown in FIG. 15A, the inner surface 78 has an osteointegration coating applied to the top surface 80 and the edges 82 of the inner surface 78. In another approach, the osteointegration coating (not shown) is only applied to the inner surface. FIG. 15B illustrates a another embodiment where a portion of the osteointegration coating 84 on the inner surface 78 is over-contoured (i.e., extends above the plane of the inner surface 78). The over-contoured coating 84 surface is compressed when the tibial base component 60 is affixed to the bone, thereby preventing micro-motion of the base component. The over-contoured coating 84 also concentrates the compressive forces on the middle of the inner surface 78.

With reference to FIGS. 16-17, the tibial base component 60 has a generally low-profile when mounted to the bone. The base component 60 is mounted to the medial surface of the tibia in order to preserve critical anatomy such as, but not limited to, medial collateral ligaments while positioning the second end 68 of the base component as close to the pivot point of the tibia. As best seen in FIG. 16, the arm portion 64 of the base component 60 is also offset from the surface of the tibia to avoid critical structure while maintaining a low profile of the base component.

The tibial base component 60 shown in FIGS. 13-17 is configured to be fixed to the medial surface of the left tibia. As those skilled in the art will appreciate, a mirror image of the base component 60 shown in FIGS. 13-17 would be fixable to the medial surface of the right tibia. Additionally, the base component may be configured to be fixed to the lateral surface of the left or right tibia. In another approach, the base component may be configured to be coupled to lateral surfaces of both the tibia and fibula. In yet another embodiment, base components may be fixed to both the lateral and medial surfaces of the left or right tibia.

FIGS. 18-19 illustrate one embodiment of an extra-articular implantable mechanical energy absorbing system 100 that is coupled to the second ends 18, 68 of the femoral and tibial base components 10, 60, respectively. Through the connections provided by the base components 10, 60, the mechanical energy absorbing system 100 can function to reduce desired forces from a knee joint. It is also to be recognized that the placement of the bases on the bones is made such that further procedures, such as a TKA, can be conducted at the joint while leaving the bases in place but after removing the absorbing system. Additionally, the absorbing system can be replaced without having to replace the base components resulting in removal of all of the wear components.

The various embodiments of the base component may be made from a wide range of materials. According to one embodiment, the base components are made from metals and alloys such as, but not limited to, Titanium, stainless steel, Cobalt Chrome. Alternatively, the base components are made from thermo-plastic materials such as, but not limited to, polyetheretherketones (PEEK). Various embodiments of the base components are rigid structures.

Figure 20A:
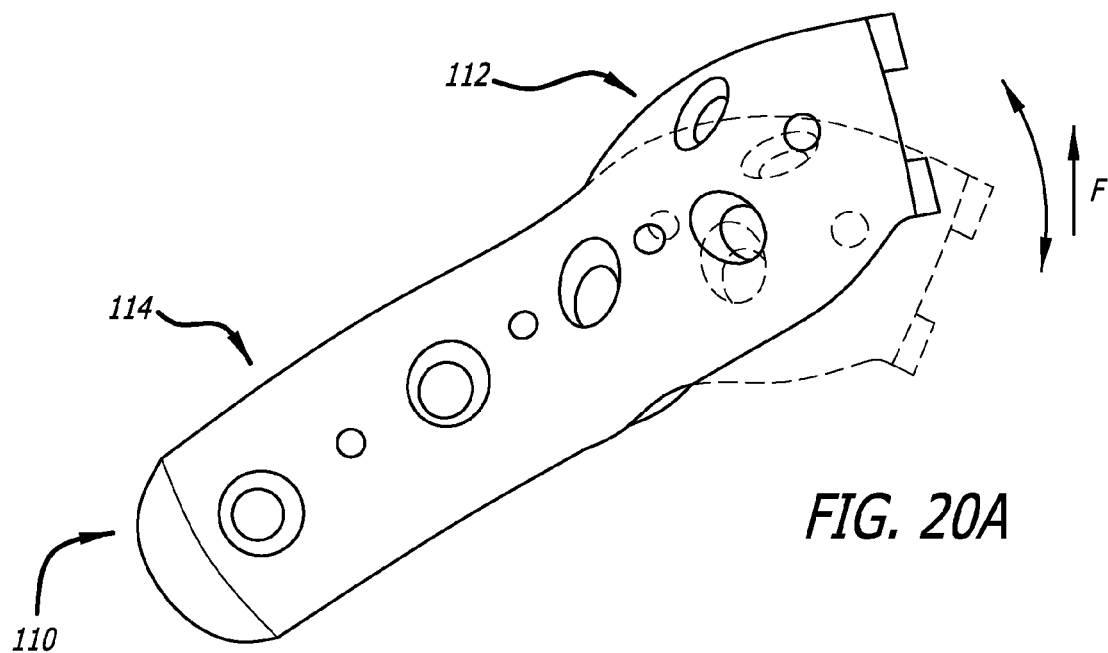
FIGS. 20A-B are side views of base components having flexible regions.
Figure 20B:
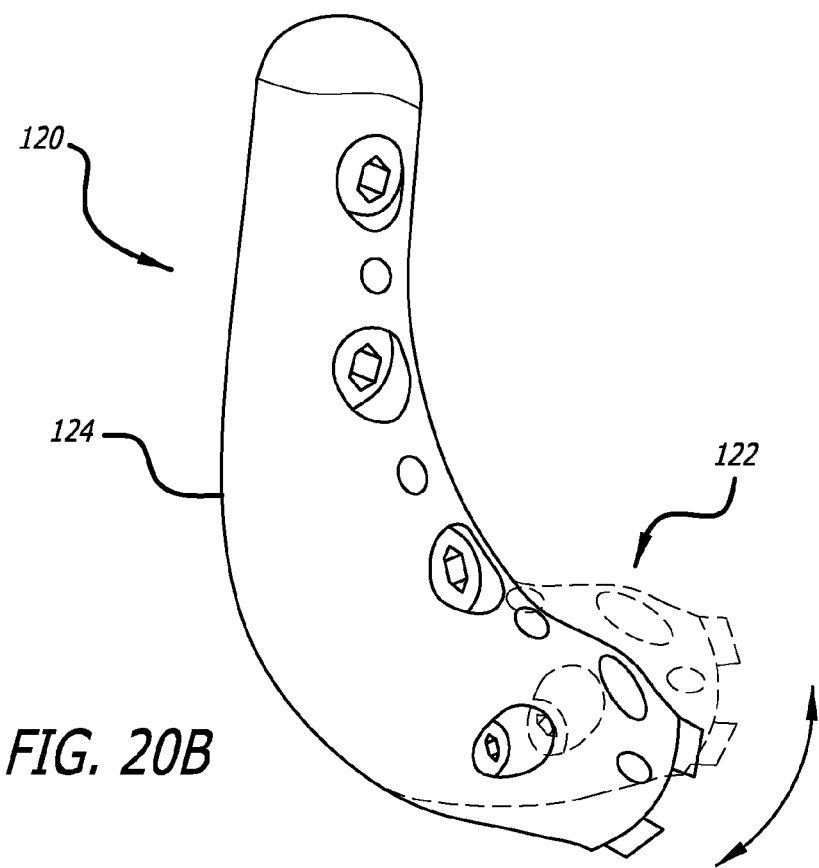

FIGS. 20A-B illustrate a tibial base component 110 and a femoral base component 120 having partially flexible regions 112, 122 for flexing and/or twisting. As shown, each base component 110, 120 includes a rigid section 114, 124 and the flexible region 112, 122. The rigid section 114, 124 of the base components 110, 120 are mountable to the bone and can include an osteointegration surface. The flexible region 112, 122 of the base components 110, 120 extends from the base and provides additional load bypass capabilities. The flexible regions 112, 114 of the base components 110, 120 apply a linear or nonlinear spring force when the flexible region is deflected. Additionally, the flexible regions 112, 122 provide adjustability in positioning of the base component on the bone by minimizing some degree of precision required to find the proper mounting location on the bone. It is also contemplated that the flexible regions 112, 122 can also be used to absorb additional forces in an overload situation to protect the base component 110, 120 stability.

Various other embodiments of bases are contemplated. Such bases can incorporate one or more of the previously described features or can embody structure separate to itself.

Figure 21A:
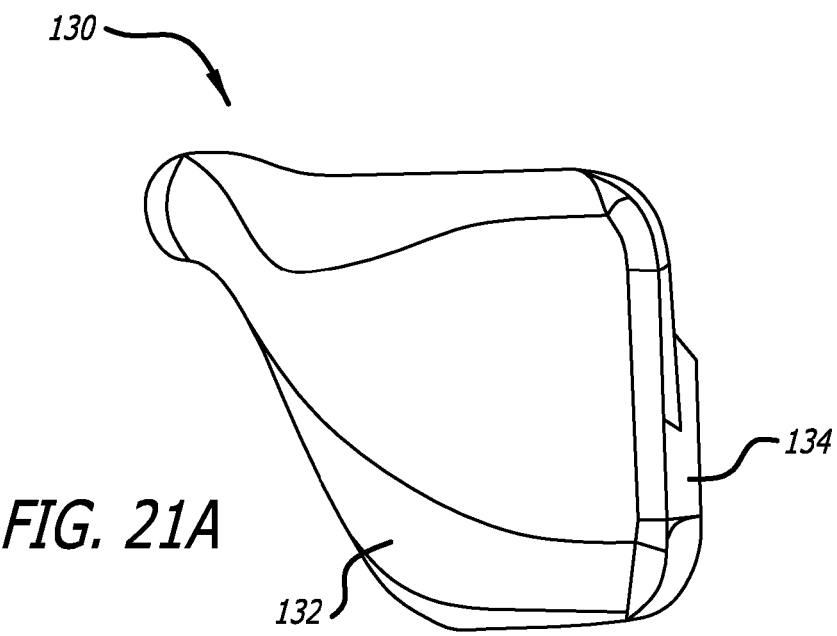
FIGS. 21A-B are perspective views of an adjustable base assembly.
Figure 21B:
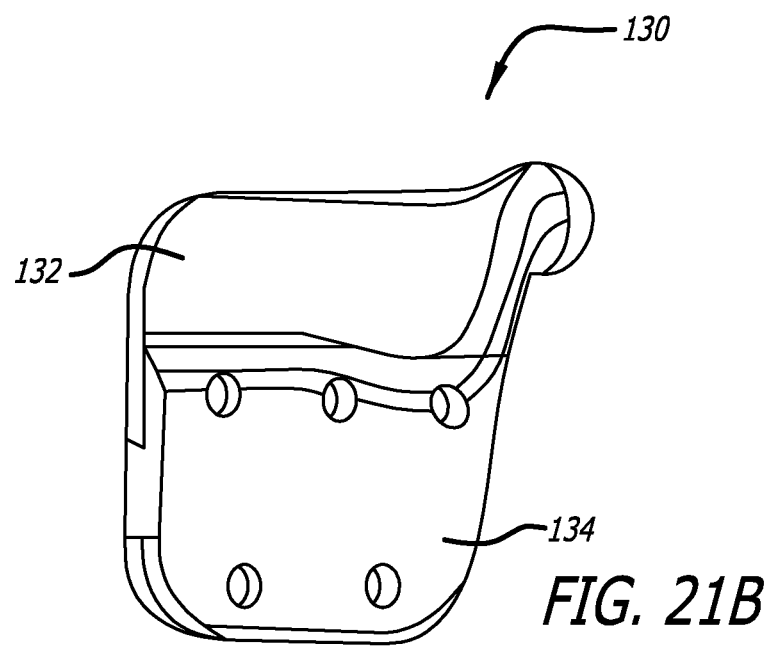

In particular, as shown in FIGS. 21A and B, one or more of the bases can include adjustment structures. Here, a base 130 can include two pieces 132, 134 which are slideable with respect to each other. A top piece 132 can be formed of a material through which fastening members can be forceably inserted without originally including one or more through holes, whereas the bottom piece 134 can include previously machined through holes. Thus, the top piece 132 can be adjusted with respect to the bottom piece and the adjusted juxtapositional relationship can be set with the fasteners employed to attach the assembly to body anatomy. Accordingly, such alterations can translate into adjusting as desired the action of absorber components of an energy absorbing assembly. It is also contemplated that the materials be selected for the bases so that they define flexible structure intended to absorb forces. Such an approach is useful where the sub-structure of an energy absorbing device includes a defined fully loaded position so that further loads are transferred to the flexible bases.

Figure 22:
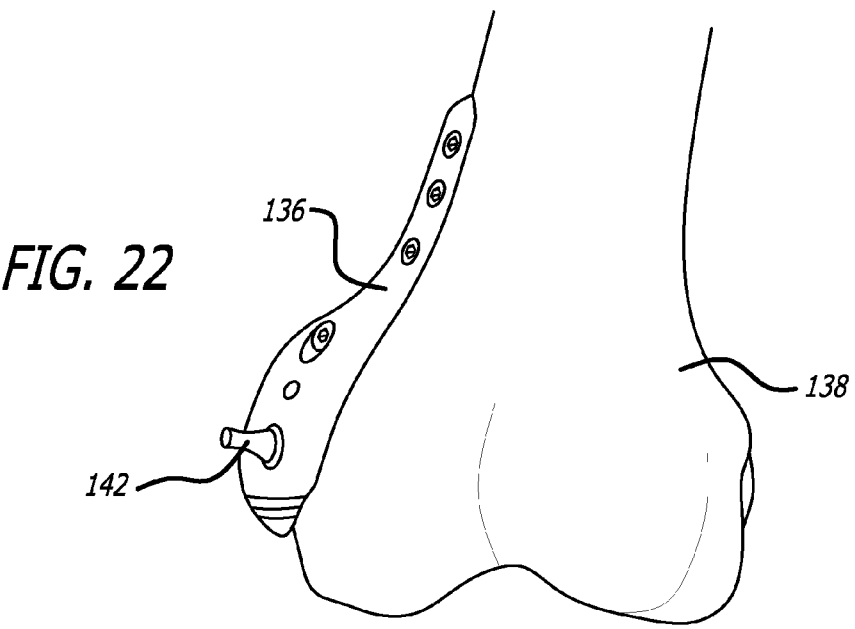
FIG. 22 is a perspective view of another embodiment of a base.
Figure 23:
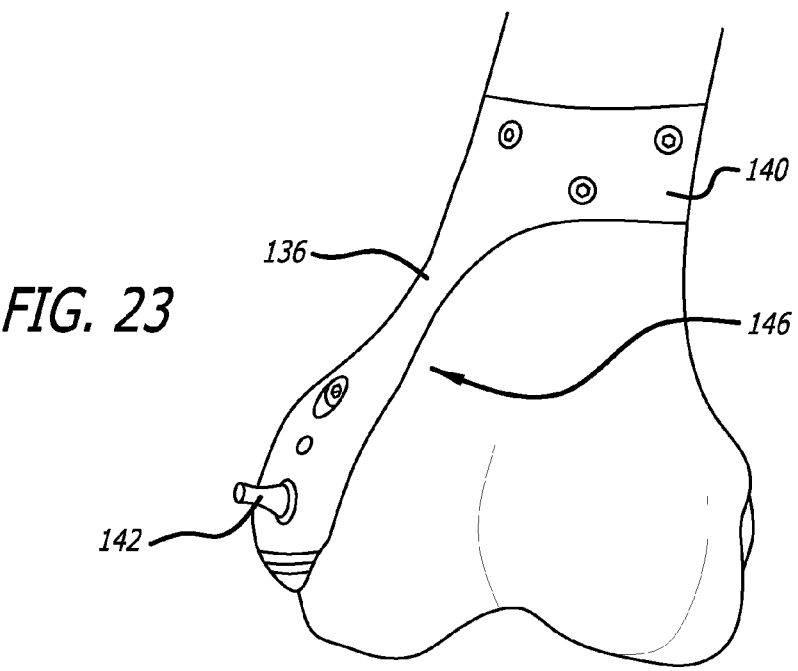
FIG. 23 is a perspective view of a first approach to a base assembly with mounting structure extending laterally on a bone.
Figure 24:
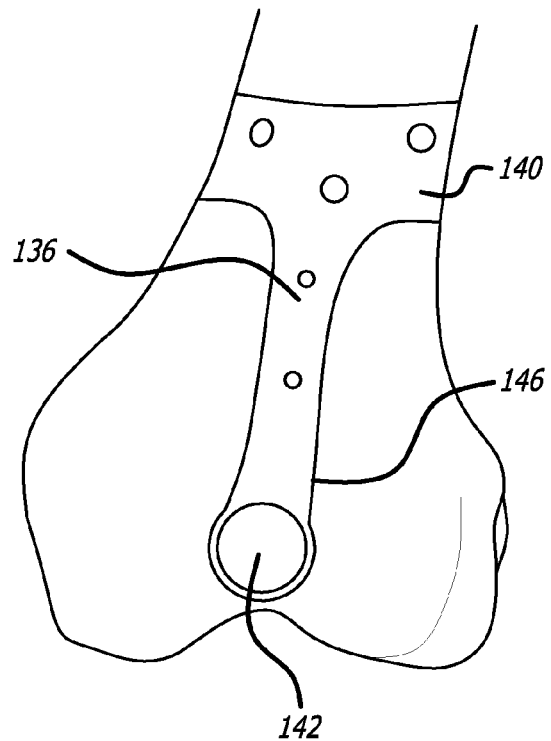
FIG. 24 is a perspective view of a second approach to a base assembly with mounting structure extending laterally.
Figure 25:
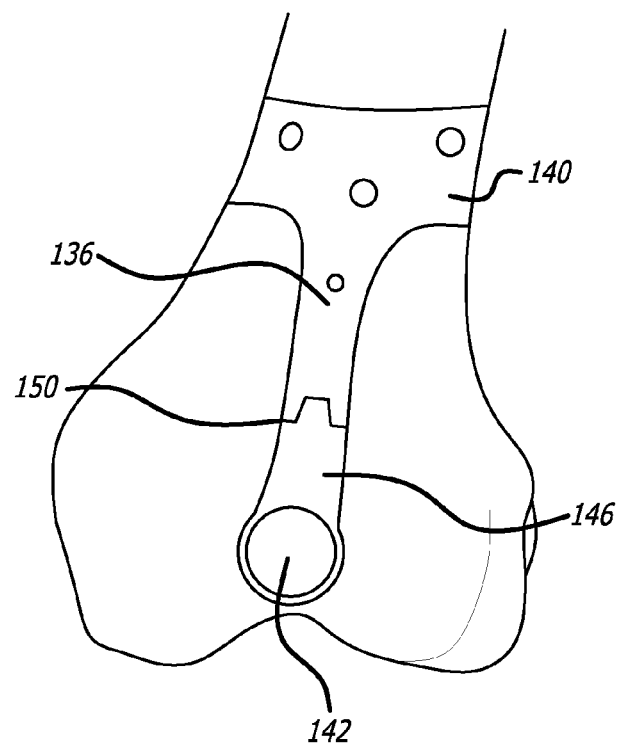
FIG. 25 is a perspective view of a third approach to a base assembly with mounting structure extending laterally.

Moreover, a base 136 can be configured to attach to cortical bone as shown in FIGS. 22-25. In these approaches, the base 136 can have an extension 138 (See FIG. 22) including mounting holes so that attachment to cortical bone is possible. Additionally, the base 136 can include a portion 140 extending about lateral surfaces of a bone to thereby be connectable to cortical bone (See FIGS. 23-25). As depicted in FIGS. 22-24, certain of these approaches can also include detachable link pin substructures 142 for releasably attaching to an energy absorbing device or other structures. Moreover, as with all disclosed approaches, these embodiments can include surfaces 146 promoting boney in-growth, such as indicated in FIGS. 23 and 24. Additionally, as specifically shown in FIG. 25, the removable pin substructure 142 can be formed in an extension 150 that is itself removable from the base 136.

Figure 26:
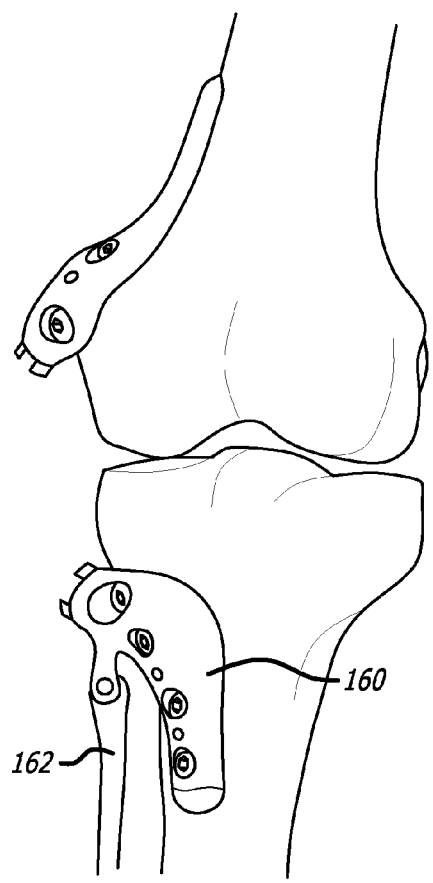
FIG. 26 is a perspective view illustrating a base component with structure supported by anatomy.
Figure 27:
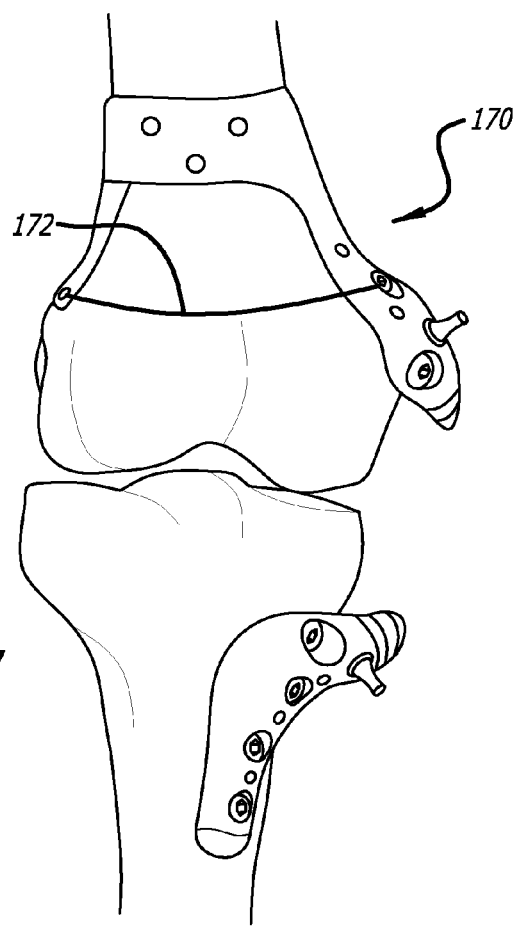
FIG. 27 is a perspective view depicting a base including multiple components.
Figure 28:
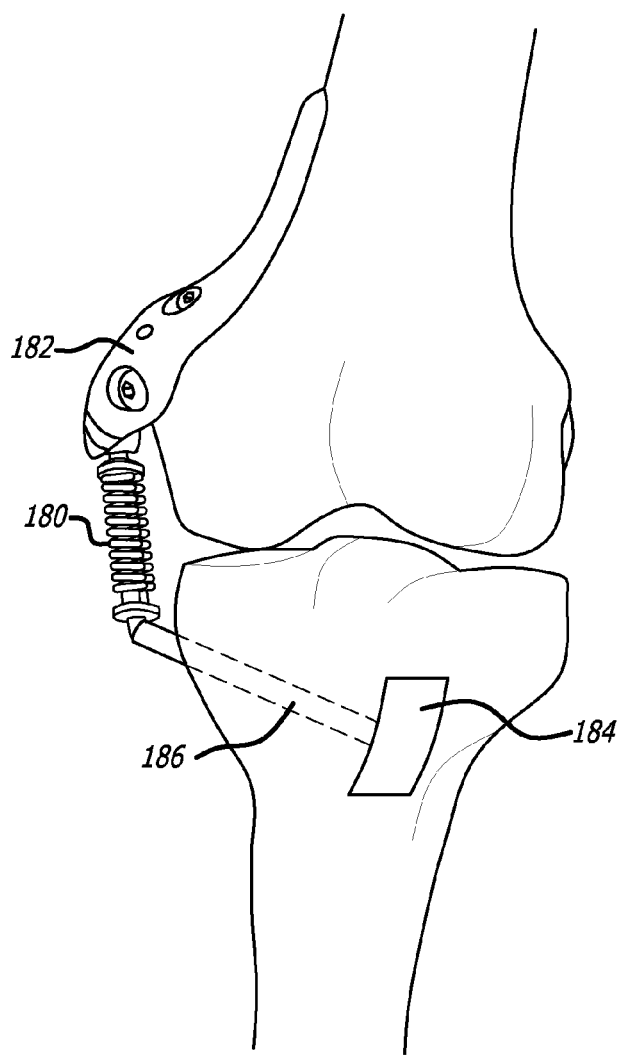
FIG. 28 is a perspective view depicting yet another approach to a supported base assembly.

In yet other approaches, the base component can include structure which relies on surrounding anatomy for additional support. For example, as shown in FIG. 26, a base 160 can include structure extending to and overlaying a fibula 162. Further, as shown in FIG. 27, a base assembly 170 can include multiple pieces attached to opposite sides of a bone and can further include a restraining cross-bar 172 extending from one of the multiple pieces to another.

Figure 29:
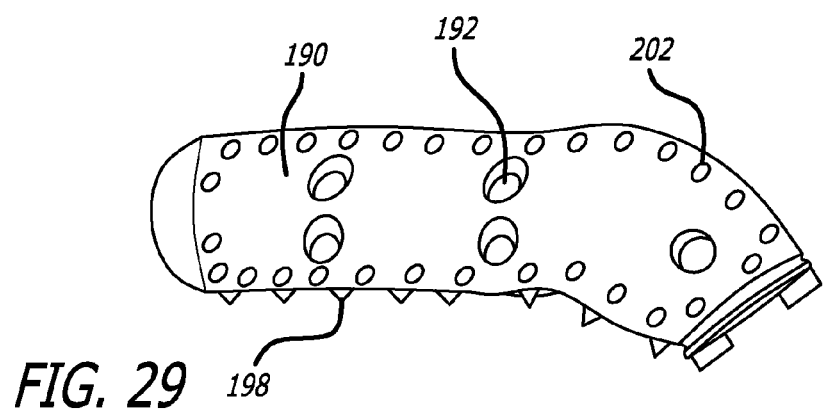
FIG. 29 is a perspective view of a base including tissue in-growth promoting substructure.

Similarly, as depicted in FIG. 29, support for an energy absorbing or other device 180 can be obtained from opposite sides of a joint. For instance, one end of the device can be supported by a laterally placed base 182 and another supported by a medially placed base 184. To do so, a rod 186 can be positioned across an interior of a bone from a laterally configured implanted device to a medial side base 184. In this way, where necessary, diseased or complex anatomy can be avoided so that a good fit to bone can be achieved.

Figure 30:
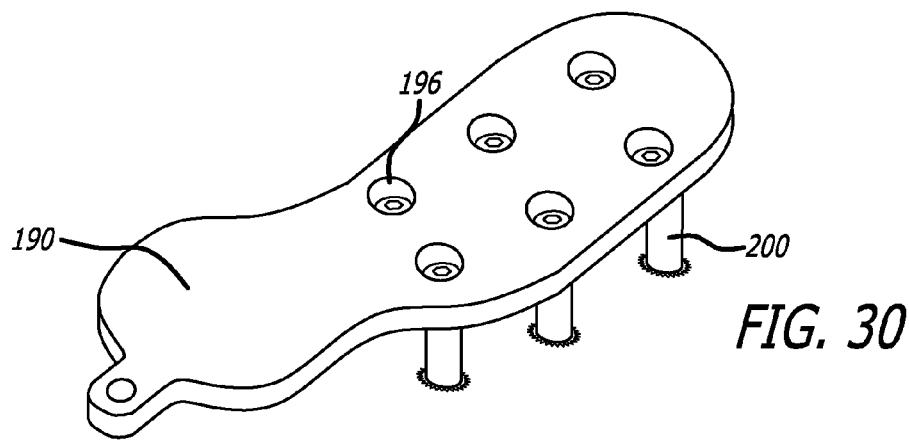
FIG. 30 is a perspective view of another base including in-growth promoting substructure.
Figure 31:
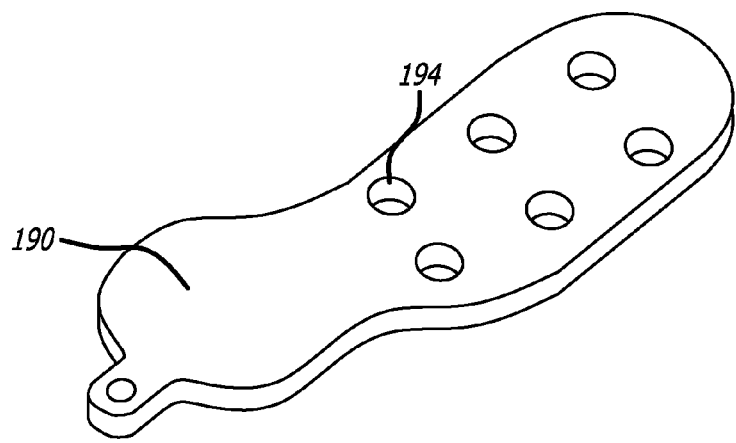
FIG. 31 is a perspective view of yet another approach to a base component.
Figure 32:
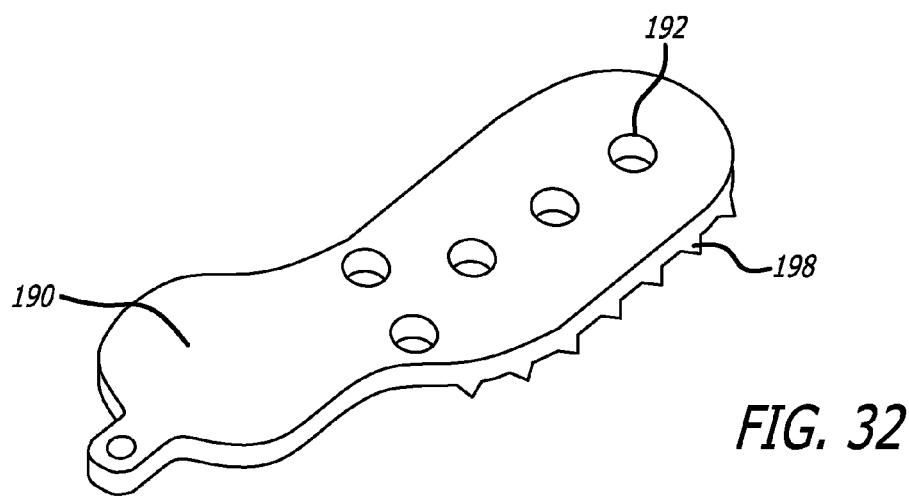
FIG. 32 is a perspective view of yet a further approach to a base component.

Turning now to FIGS. 29-32, yet further contemplated embodiments of bases 190 are illustrated. Such bases can have simple through holes 192 (FIGS. 29 and 32) for fastening members or such holes can include countersinks 194 (FIG. 31). Additionally, the fastening holes can define screw head sockets 196 as shown in FIG. 30. Moreover, the contemplated bases can embody various approaches for accomplishing connection to the bone such as by including spikes 198 (FIGS. 29 and 32) or rotatable spurs 200 (FIG. 30). Furthermore, the bases 190 can include small holes 202 such as those having a diameter of less than 1 mm for boney, interlocking in-growth (FIG. 29).

Figure 33:
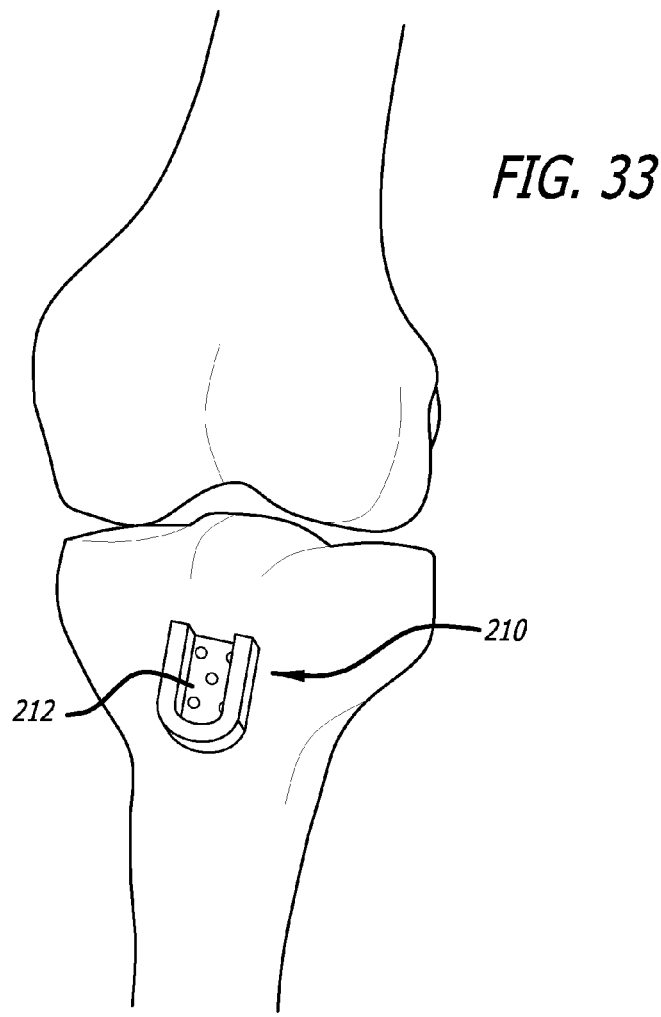
FIG. 33 is a perspective view of a base component including a slotted portion.
Figure 34:
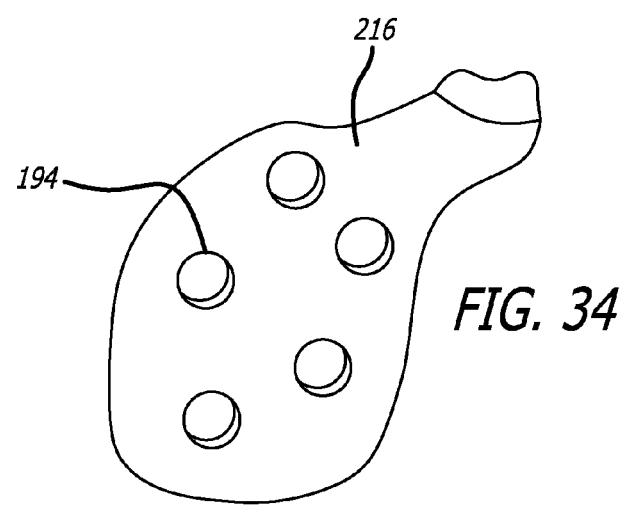
FIG. 34 is a perspective view depicting a base component with coded holes.

Finally, as shown in FIG. 33, the base 210 can include a slotted region 212 for receiving corresponding structures. Also, the holes 214 formed on a base 216 can be numbered or otherwise identified to assist a physician in selecting proper fastening members.

The various embodiments described above are provided by way of illustration only and should not be construed to limit the claimed invention. Those skilled in the art will readily recognize various modifications and changes that may be made to the claimed invention without following the example embodiments and applications illustrated and described herein, and without departing from the true spirit and scope of the claimed invention, which is set forth in the following claims. In that regard, various features from certain of the disclosed embodiments can be incorporated into other of the disclosed embodiments to provide desired structure.

What is claimed:

1. An implantable mechanical extra-articular system for a knee joint including a joint capsule, comprising:
    an absorber, the absorber absorbs a predetermined compression load applied to the knee joint; and
    a base having two ends, an upper surface, an inner surface opposite the upper surface and a mounting surface,
    wherein the inner surface includes a bone contacting surface configured to engage and attach to exterior surfaces of bone, and a non-contacting surface displaced vertically from the bone contacting surface and closer towards a portion of the upper surface overlaying the non-contacting surface so as to be offset from exterior surfaces of the bone,
    wherein the mounting surface alone is configured to operatively engage and connect to the absorber, and wherein the mounting surface is located at one of the two ends with all portions of the mounting surface elevated above the bone surface to position the absorber outside the joint capsule.

2. The system of claim 1, further comprising a plurality of openings positioned on the base, wherein the openings define bores having differing trajectories and are sized to receive fastening members.

3. The system of claim 1, wherein bone promoting treatment is applied to the bone contacting surface, the treatment being selected from the group consisting essentially of bone morphogenic protein 2, hydroxyapatite, titanium beads, or cobalt chrome beads.

4. The system of claim 1, wherein a bone promoting treatment is applied to surfaces of the base, the treatment altering the surface roughness, porosity or chemical composition at these surfaces.

5. The system of claim 1, further comprising a bore positioned at an end of the base, wherein the bore is oriented generally perpendicular to the end of the base.

6. The system of claim 5, wherein an opening of the bore is tapered inward.

7. The system of claim 5, further comprising a removable sleeve positioned within the bore.

8. The system of claim 7, further comprising a post connected to the absorber, wherein the post pressed into the sleeve within the bore forms a taper lock.

9. The system of claim 5, further comprising one or more alignment members protruding from the end of the base.

10. An implantable extra-articular mechanical energy absorbing system for a knee joint including a joint capsule, comprising:
    an absorber, the absorber absorbs a predetermined compression load applied to the knee joint; and
    a base including a low-profile body having a mounting portion configured to be operatively connected to the absorber, a bone contacting surface conforming to an exterior surface of a bone, an upper surface, an inner surface opposite the upper surface, a mounting surface and a non-contacting surface,
    wherein the mounting portion is elevated above the bone surface to position the absorber outside the joint capsule and wherein the mounting surface alone is configured to operatively engage and connect to the absorber.

11. The system of claim 10, further comprising one or more projections extending from the bone contacting surface.

12. The system of claim 10, further comprising one or more through holes positioned along the low-profile body, the through holes configured to receive fastening members.

13. The system of claim 10, wherein osteointegration is promoted by a coating applied to the bone contacting surface.

14. The system of claim 10, wherein osteointegration is promoted by providing the base contacting surface with a roughened surface.

15. The system of claim 10, wherein the bone contacting surface is contoured for a medial portion of a femur or a tibia.

16. The system of claim 10, wherein the bone contacting surface is contoured for a femur or tibia.

17. The system of claim 10, wherein the selected surface area is about 39mm$^2$ or greater.

18. The system of claim 10, wherein the bone response is mechanical interlocking into the base.

19. The system of claim 10, wherein the bone response is chemical bonding onto the base.

20. The system of claim 10, wherein the system is configured to have a shear strength of about 3MPa or greater without support from fasteners after porous ingrowth of bone.

21. The system of claim 10, wherein the system is configured to have a shear strength greater than the shear stress applied by the forces of the absorber after porous ingrowth of bone.

22. An implantable extra articular system for a knee joint including a joint capsule, comprising:
    a link which absorbs a compression load applied to the knee joint; and
    a base having two ends and including an elongated periosteum contacting portion configured to conform and extend along an exterior surface of a femur, a curved portion extending transversely away from the elongated portion, and a mounting portion, the mounting portion alone being configured to operatively engage and connect to the link, wherein the mounting portion is located at one of the two ends with all portions of the mounting surface offset from and overlying exterior surfaces of the bone and wherein the mounting portion is elevated above the bone surface to position the link outside the joint capsule.

23. The system of claim 22, further comprising one or more through holes positioned along the base, the through holes configured to receive fastening members.

24. An implantable mechanical extra-articular system for a knee joint including a joint capsule, comprising:
    a link which absorbs a compression load applied to the knee joint; and
    a base having a mounting end, an upper surface and an inner surface opposite the upper surface, wherein the inner surface includes a bone contacting surface configured to engage and attach to exterior surfaces of bone, and a non-contacting surface configured to be displaced from the bone, wherein the non-contacting surface is adjacent the mounting end;
    a mounting surface on the mounting end configured to operatively connect to the link, wherein the mounting surface is elevated above the bone surface to position the link outside the joint capsule;
    a bore formed in the mounting surface of the base, wherein the bore is oriented generally perpendicular to the mounting surface of the base, wherein an opening of the bore is tapered inward; and
    a post connected to the link, wherein the post and the bore form a lock.

25. The system of claim 24, wherein the post and bore form a taper lock connection.

* * * * *